United States Patent

Gadwood et al.

Patent Number: 5,736,545
Date of Patent: Apr. 7, 1998

[54] AZOLYL PIPERAZINYL PHENYL OXAZOLIDINONE ANTIMICROBIALS

[75] Inventors: Robert C. Gadwood; Michael Robert Barbachyn; Dana Scott Toops; Herman Walden Smith; Valerie Ann Vaillancourt, all of Kalamazoo, Mich.

[73] Assignee: Pharmacia & Upjohn Company, Kalamazoo, Mich.

[21] Appl. No.: 803,469

[22] Filed: Feb. 20, 1997

Related U.S. Application Data

[60] Provisional application No. 60/012,316 Feb. 26, 1996.

[51] Int. Cl.⁶ ............... A61K 31/495; C07D 413/14; C07D 417/14; C07D 419/14
[52] U.S. Cl. ............... 514/252; 514/254; 544/368; 544/369
[58] Field of Search ............... 544/368, 369; 514/252, 254

[56] References Cited

U.S. PATENT DOCUMENTS

| | | | |
|---|---|---|---|
| 4,801,600 | 1/1989 | Wang et al. | 548/229 |
| 4,921,869 | 5/1990 | Wang et al. | 514/376 |
| 4,948,801 | 8/1990 | Carlson et al. | 514/307 |
| 4,977,173 | 12/1990 | Brittelli et al. | 514/376 |
| 5,254,577 | 10/1993 | Carlson et al. | 514/376 |
| 5,547,950 | 8/1996 | Hutchinson et al. | 514/252 |
| 5,652,238 | 7/1997 | Brickner et al. | 514/235.8 |

FOREIGN PATENT DOCUMENTS

| | | |
|---|---|---|
| WO 93/23384 | 11/1993 | WIPO . |
| WO 95/07271 | 3/1995 | WIPO . |
| WO 95/14684 | 6/1995 | WIPO . |

OTHER PUBLICATIONS

Barbachyn et al, *Chemical Abstracts*, vol. 123, No. 256742 (Abstract for WO 9507271 Mar. 16, 1995).

Journal of Medicinal Chemistry, vol. 39, No. 3, 2 Feb. 1996, Washington US, pp. 673–679, Steven J. Brickner et al.: "Synthesis and Antibacterial Activity of U–100592 and U–100706, Two Oxazolidinone Antibacterial Agents for the Potential Treatment of Multidrug–Resistant Gram–Positive Bacterial Infections."

*Primary Examiner*—Emily Bernhardt
*Attorney, Agent, or Firm*—Donald L. Corneglio; Lucy X. Yang

[57] ABSTRACT

Compounds useful in the preparation of pharmaceutical preparations for the treatment of microbial infection where such compounds are of structural Formula I

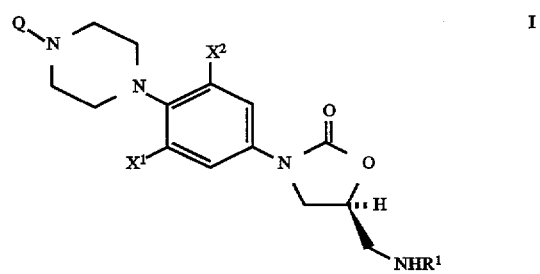

or pharmaceutically acceptable salts thereof wherein: $R^1$ is —CHO, —COCH$_3$, —COCHCl$_2$, —COCHF$_2$, —CO$_2$CH$_3$, —SO$_2$CH$_3$, or —COCH$_2$OH; $X^1$ and $X^2$ are independently H, F, or Cl; and Q is a five membered ring heterocycle (azolyl ring) of the general form:

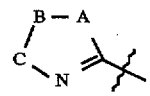

wherein A, B, and C are independently oxygen (O), nitrogen (N), sulfur (S) or Carbon (C). In all cases, the piperazine nitrogen atom is attached at the carbon atom of the carbon-nitrogen double bond.

8 Claims, No Drawings

AZOLYL PIPERAZINYL PHENYL OXAZOLIDINONE ANTIMICROBIALS

CROSS-REFERENCE TO RELATED APPLICATION

This application claims the benefit of the following provisional application: U.S. Ser. No. 60/012,316, filed Feb. 26, 1996, under 35 USC 119(e)(i).

BACKGROUND OF THE INVENTION

The subject invention discloses azolyl piperazinyl phenyl oxazolidinone derivatives. The compounds are useful antimicrobial agents, effective against a number of human and veterinary pathogens, including gram-positive aerobic bacteria such as multiply-resistant *staphylococci*, *streptococci* and *enterococci*, as well as anaerobic organisms such as *Bacteroides spp.*, and acid-fast organisms such as *Mycobacterium tuberculosis*.

Information Disclosure

The present compounds are similar to piperazine-containing structures such as those disclosed in WO93/23384, Nov. 25, 1987 (PCT/US93/03570) except that the distal nitrogen atom is substituted with an azolyl ring system. The appended azolyl ring imparts potent antibacterial activity to the piperazinyl phenyl oxazolidinone template.

WO95/14684, Jun. 1, 1995 (PCT/US94/10582) discloses esters of the oxazolidinone, piperazine ring structures disclosed in the above PCT application.

WO95/07271, Mar. 16, 1995 (PCT/US94/08904) discloses oxazolidinones although containing morpholine and thiomorpholine instead of the subject piperazine.

Other earlier publications in the area of oxazolidinones are U.S. Pat. Nos. 4,801,600, 4,921,869, EPA 0352781 (Jan. 31, 1989) and EPA 0316594 (May 24, 1989) all assigned to E. I. DuPont De Nemours and Company which are cited here to exemplify the state of the art.

SUMMARY OF THE INVENTION

In one aspect the subject invention is a compound of structural Formula I:

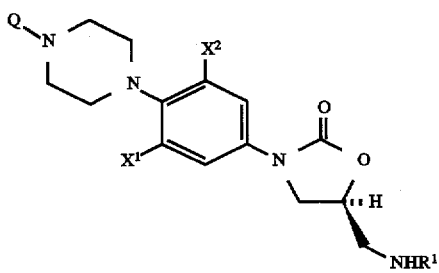

I or pharmaceutically acceptable salts thereof wherein:
$R^1$ is (a) —CHO,
(b) —COCH$_3$,
(c) —COCHCl$_2$,
(d) —COCHF$_2$,
(e) —CO$_2$CH$_3$,
(f) —SO$_2$CH$_3$, or
(g) —COCH$_2$OH;
$X^1$ and $X^2$ are independently H, F, or Cl; and
Q is a five membered ring heterocycle (azolyl ring) of the general form:

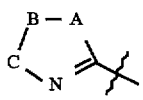

wherein A, B, and C are independently oxygen (O), nitrogen (N), sulfur (S) or Carbon (C). In all cases, the piperazine nitrogen atom is attached at the carbon atom of the carbon-nitrogen double bond. This heterocycle confers potent antibacterial activity which is not present in the parent oxazolidinone (I where Q is hydrogen (H)).

More specifically, in the present invention, Q is:

(a) oxazole:

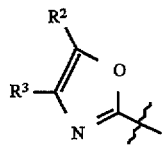

II (b) oxazol-4-one:

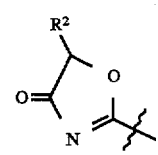

III (c) 4,5-dihydrooxazole:

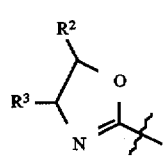

IV (d) benzoxazole:

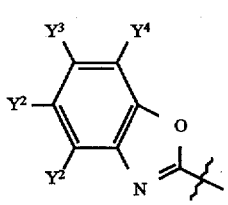

V (e) 1,3,4-oxadiazole:

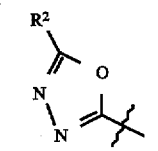

VI (f) 1,2,4-oxadiazole (attached to piperazine at C5):

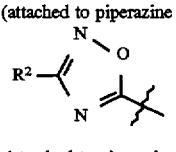

VII (g) 1,2,4-oxadiazole (attached to piperazine at C3):

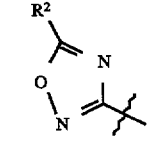

VIII

-continued (h) 1,2,4-oxadiazol-5-one: 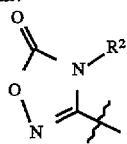 IX (i) 1,3,4-oxathiazol-2-one: 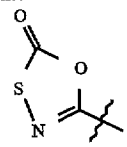 X (j) thiazole: 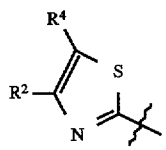 XI (k) benzothiazole: 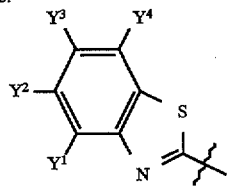 XII (l) thiazol-4-one: 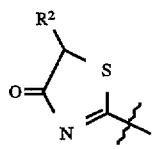 XIII (m) thiazoledione: 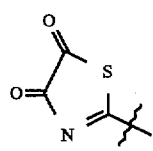 XIV (n) thiazoline: 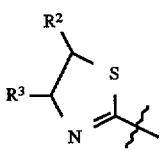 XV (o) 1,3,4-thiadiazole: 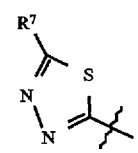 XVI (p) 1,3,4-thiadiazol-2-one: 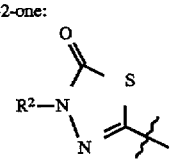 XVII -continued (q) 1,2,4-thiadiazole: 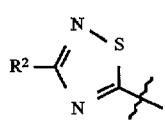 XVIII (r) 1,2,4-thiadiazol-3-one: 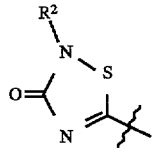 XIX (s) 1,2,5-thiadiazole: 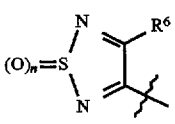 XX (t) 1,2,3,4-thiatriazole: 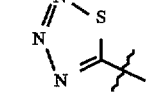 XXI (u) 1,2,4-dithiazolone: 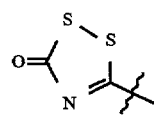 XXII (v) imidazole: 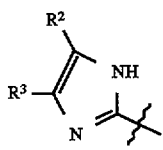 XXIII (w) benzimidazole: 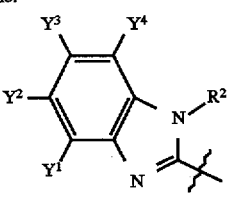 XXIV (x) imidazol-4-one: 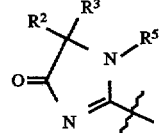 XXV (y) 1,2,4-triazole (Type 1): 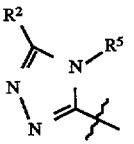 XXVI -continued (z) 1,2,4-triazole (Type 2):  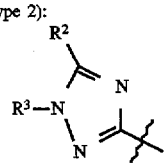

(aa) 1,2,4-triazole (Type 3):  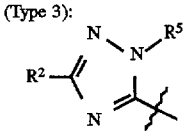

(bb) 1,2,4-triazolone:  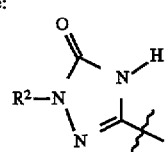

(cc) 1,2,3-triazole:  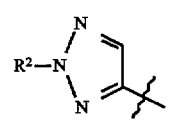

(dd) tetrazole (Type 1):  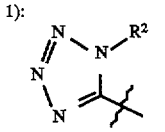

(ee) tetrazole (Type 2):  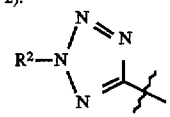

(ff) isoindol-7-ones:  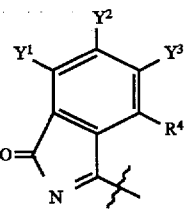

(gg) pyrazol-3-one:  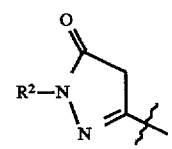

(hh) pyrazoline:  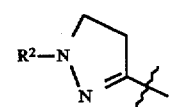

(ii) pyrazole:  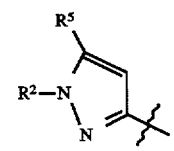

-continued (jj) indazole:  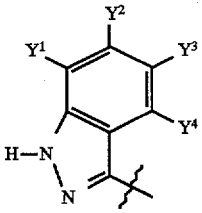

(kk) benzoisothiazole:  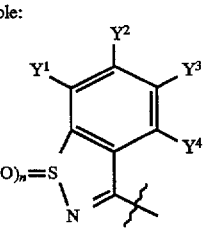

(ll) isoxazole:  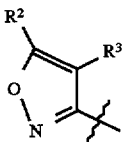

(mm) benzisoxazole:  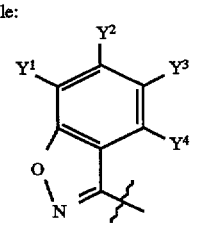

or (nn) 1,2,3-oxathiazole-1-oxide:  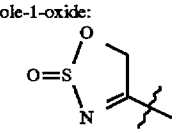

wherein $R^2$ and $R^3$ are independently
   (a) H— (except where Q is formula XXXI or XXXII),
   (b) $(C_1-C_8)$alkyl-,
   (c) $(C_3-C_5$ cycloalkyl)—, or
   (d) phenyl;
or $R^2$ and $R^3$ taken together are —$CH_2$—$(CH_2)_m$—;
wherein $R^4$ is
   (a) H—,
   (b) $(C_1-C_8$ alkyl)—,
   (c) $(C_3-C_5$ cycloalkyl)—,
   (d) phenyl-,
   (e) $O_2N$—, or
   (f) $CH_3CH_2OC(O)$—;
or $R^2$ and $R^4$ taken together are —$CH_2$—$(CH_2)_m$—;
wherein $R^5$ is
   (a) H—,
   (b) $(C_1-C_8$ alkyl)—,
   (c) $(C_3-C_5$ cycloalkyl)—, or
   (d) phenyl-;
wherein $R^6$ is
   (a) H—,
   (b) $(C_1-C_8$ alkyl)—,
   (c) $(C_3-C_5$ cycloalkyl)—,
   (d) phenyl-, or
   (e) $OR^2$;

wherein R⁷ is
  (a) H—,
  (b) (C₁-C₈ alkyl)—,
  (c) (C₃-C₅ cycloalkyl)—,
  (d) phenyl-,
  (e) H₂N—,
  (f) H₂NCO—,
  (g) R₅OCO—,
  (h) NC—,
  (i) R₅S—,
  (j) R₅O—, or
  (k) CF₃;

with the following provisos:
where Q is XXV, R² and R³ is H, R⁵ is other than methyl;
where Q is XVIII, R² is other than phenyl;
wherein m is zero (0) to five (5), inclusive;
wherein n is zero (0) to two (2), inclusive;
wherein Y¹, Y², Y³, and Y⁴ are independently
  (a) H,
  (b) NO₂, or
  (c) F, Cl, or Br.

In another aspect, the subject invention is directed toward a method for treating microbial infections in patients by administering to a patient in need thereof an effective amount of a compound of Formula I as described above. The compound can be administered in a pharmaceutical composition either orally, parenterally or topically. Preferably, the compound is administered in an amount of from about 0.1 to about 100 mg/kg of body weight/day, more preferably, from about 3.0 to about 50 mg/kg of body weight/day.

DETAILED DESCRIPTION OF THE INVENTION

The X¹ and X² groups can be independently either hydrogen atoms or the defined halogen atoms in a variety of substitution patterns. The X¹ and X² substituents are preferably both fluorine and, more preferably, one fluorine and one H.

The preferred absolute configuration at C-5 of the oxazolidinone ring of compounds claimed in this invention is as represented in the structure of Formula I. This absolute configuration is called (S) under the Cahn-Ingold-Prelog nomenclature system. It is this (S)-enantiomer which is antibacterially active. The racemic mixture is useful in the same way and for the same purpose as the pure (S)-enantiomer; the difference is that twice as much racemic material must be used to produce the same antibacterial effect. It will be apparent to one skilled in the art that selected azolyl ring systems may have additional chiral centers present to give diastereomers. These diastereomers, in racemic and enantiomerically enriched forms, are also within the scope of the compounds of Formula I.

Methods for preparing oxazolidinones of Formula I are depicted in the following pages. All of the described compounds can be made from the N—(1-piperazinylphenyl)-2-oxo-5-oxazolidines (XLII) which in turn can be prepared as described in PCT/US93/03570. It will be apparent to those skilled in the art that the described synthetic procedures are merely representative in nature and that alternative procedures are feasible and may be preferred in some cases.

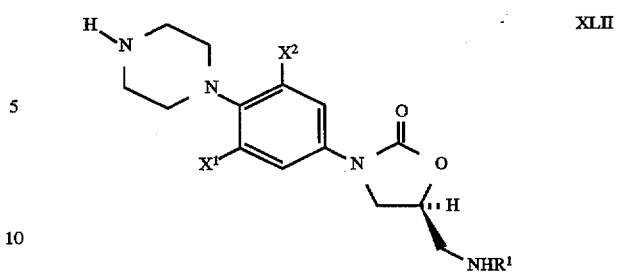

Oxazoles (I-A) of the present invention (structure I where Q is moiety II) are made by the reaction of 2-chlorooxazoles (XLIII) with XLII according to procedures outlined by I. J. Turchi (*Chem. Rev.*, 1975, 75, 389). 2-Chlorooxazoles are prepared by methods well known in the literature or are obtained commercially.

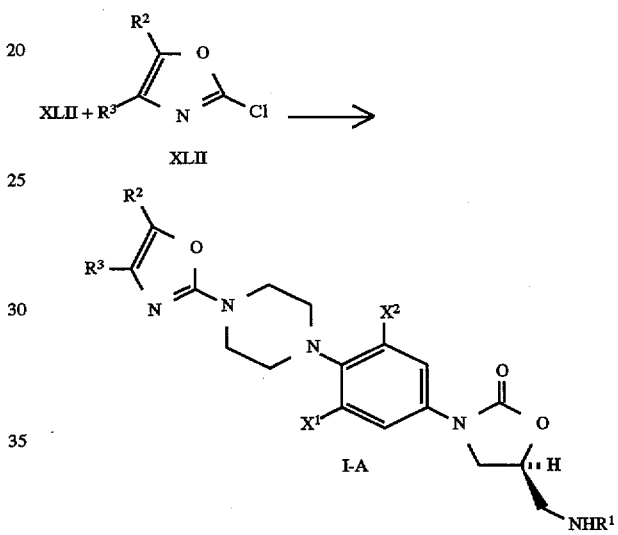

Alternatively, compound XLII is reacted with potassium cyanate to afford the urea (XLIV) which is then converted to the oxazole by reaction with various bromoketones according to the procedure of R. Gompper (*Chem. Ber.*, 1959, 92, 1944).

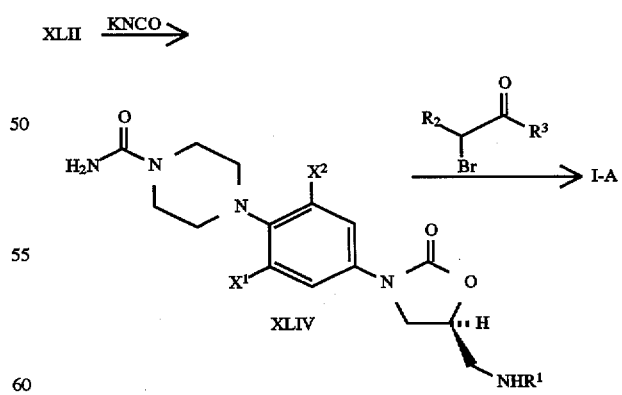

Oxazol-4-ones (I-B) of the present invention (structure I where Q is moiety III) are made by reaction of XLII with cyanogen bromide to afford the cyanamide XLV followed by reaction with α-hydroxyesters to produce I-B. These procedures are based on those reported by C. F. Howell (*J. Org. Chem.*, 1962, 27, 1679).

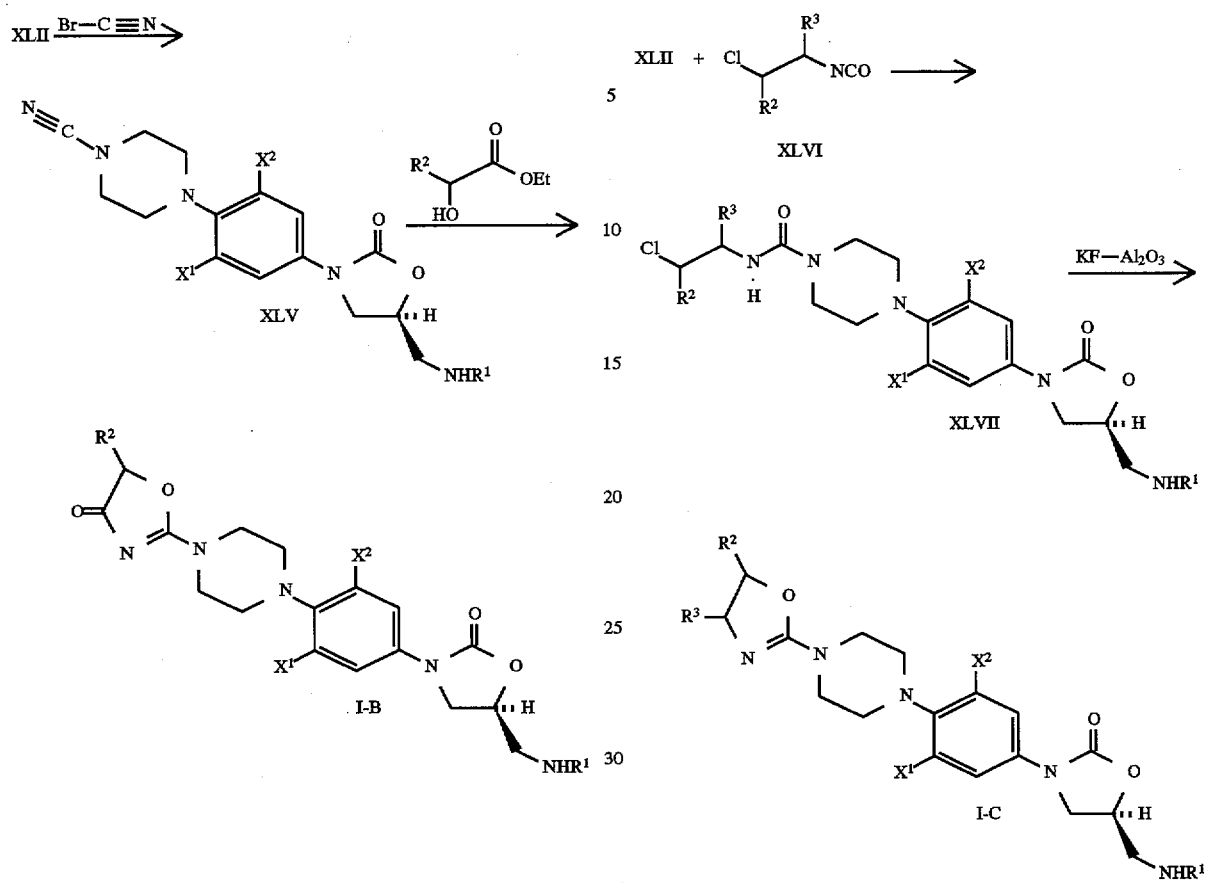

4,5-Dihydrooxazoles (I-C) of the present invention (structure I where Q is moiety IV) are made by reaction of XLII with 2-chloroethylisocyanates (XLVI) to produce an intermediate urea (XLVII) which is then converted to I-C by treatment with a mild base such as potassium fluoride absorbed onto alumina. This method has been disclosed by W. C. Wong (*Bioorganic Med. Chem. Lett.*, 1994, 4, 2317). The required 2-chloroethylisocyanates are prepared by methods known in the literature or are obtained from commercial sources.

Benzoxazoles (I-D) of the present invention (structure I where Q is moiety V) are made by reaction of XLII with 2-chlorobenzoxazoles (XLVIII) according to the procedures of R. Benassi (*J. Chem. Soc. Perkin Trans. II*, 1985, 1513).

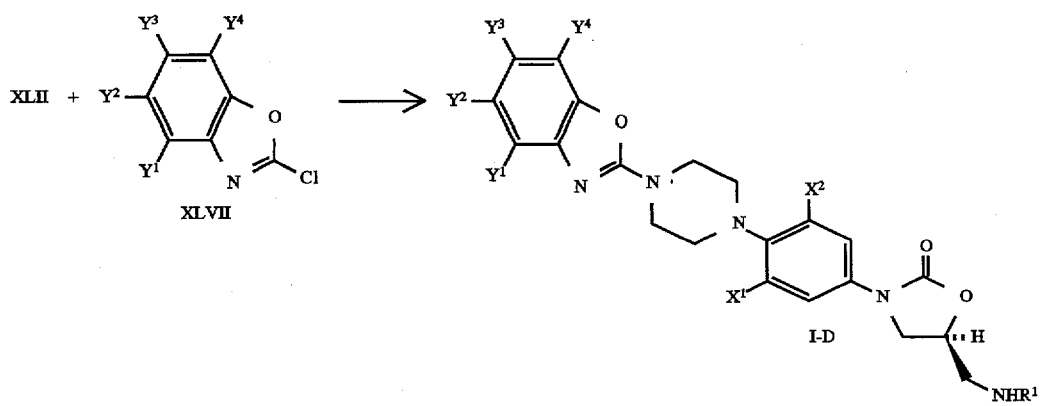

1,3,4-Oxadiazoles (I-E) of the present invention (structure I where Q is moiety VI) are made by reaction of XLII with 2-chloro-1,3,4-oxadiazoles (XLIX) according to the procedure of R. Madhavan (*Ind. J. Chem.*, 1969, 7, 760). The 2-chloro-1,3,4-oxadiazoles are prepared by methods known in the literature.

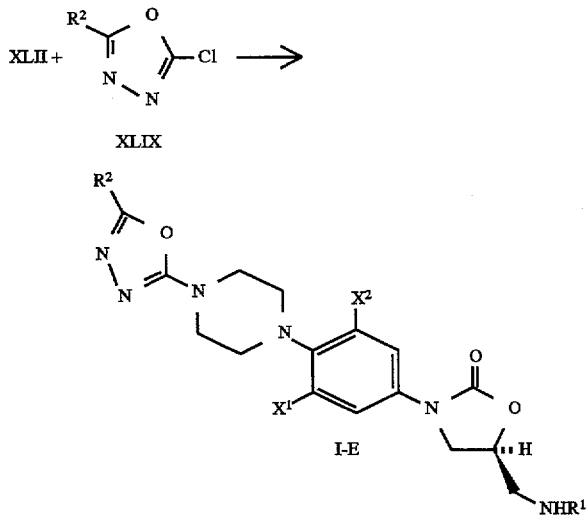

1,2,4-Oxadiazoles (I-F) of the present invention (structure I where Q is moiety VII) are made by reaction of XLII with 5-trichloromethyl-1,2,4-oxadiazoles (L) according to the procedures of S. Yuragi (*Chem. Pharm. Bull.* 1973, 21, 1641). The 5-trichloromethyl-1,2,4-oxadiazoles are prepared by procedures disclosed by S. Yuragi in the same publication.

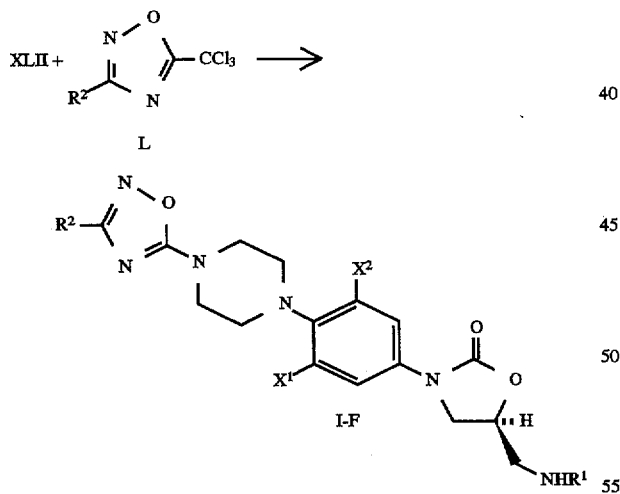

1,2,4-Oxadiazoles (I-G) of the present invention (structure I where Q is moiety VIII) are isomeric with 1,2,4-oxadiazoles I-F and differ only in the point of attachment of the piperazine to the oxadiazole ring. 1,2,4-Oxadiazoles I-G are made by reaction of XLII with 3-bromo-1,2,4-oxadiazoles LI according to the procedures of P. Choi (*Tetrahedron Lett.*, 1982, 23, 125).

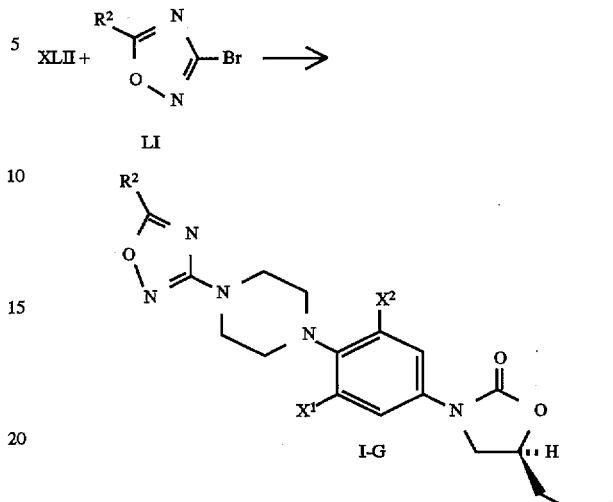

1,2,4-Oxadiazol-5-ones I-H of the present invention (structure I where Q is moiety IX) are prepared by reaction of XLII with ethoxycarbonylisothiocyanate to afford the thiourea LII, methylation to the isothiourea LIII, and then reaction with hydroxylamine. These methods have been reported by P. R. Atkins (*J. Chem. Soc. Perkin Trans. I* 1973, 2644).

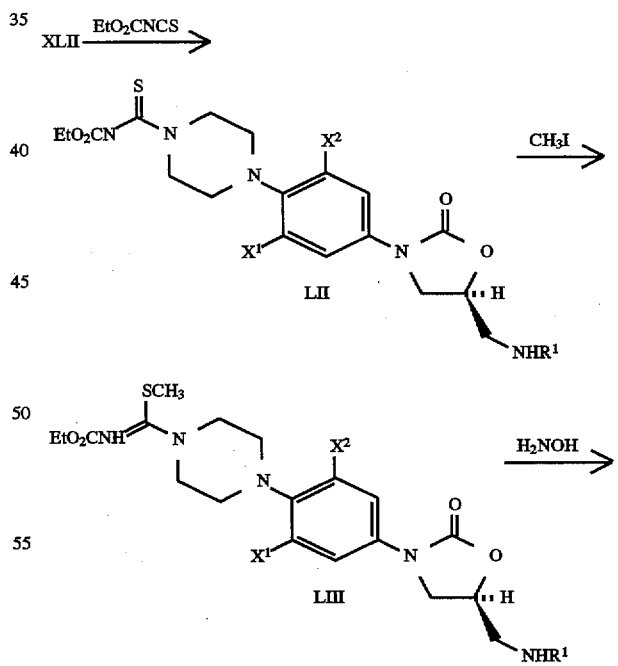

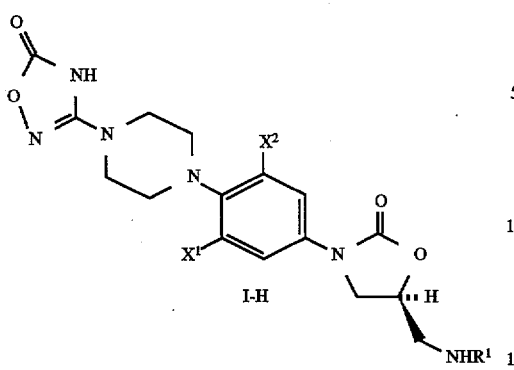

I-H 1,3,4-Oxathiazol-2-ones (I-I) of the present invention (structure I where Q is moiety X) are made by reaction of the urea XLIV with chlorocarbonylsulfenyl chloride according to the procedures of I. T. Hogan (*Tetrahedron* 1984, 40, 681).

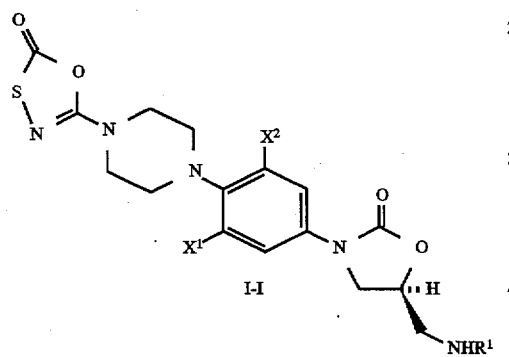

I-I

Thiazoles (I-J) of the present invention (structure I where Q is structure XI) are made by reaction of XLII with 2-bromothiazoles (LIV) according to the procedure of Bonzom (*Bull. Soc. Chim. Fr.,* 1963, 2582). The required 2-bromothiazoles can be prepared according to methods well known in the literature.

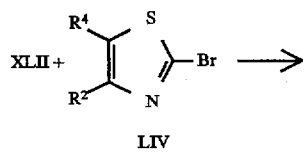

LIV

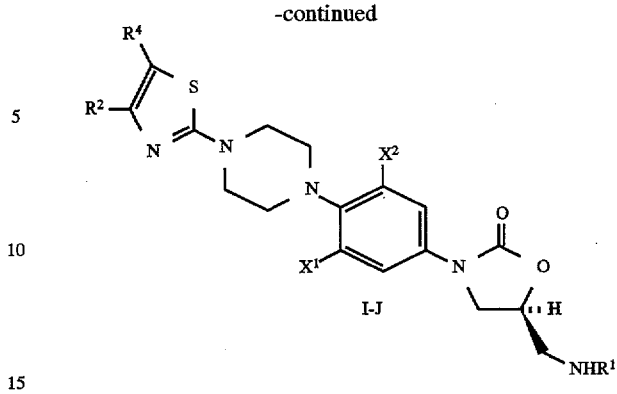

I-J

Benzothiazoles (I-K) of the present invention (structure I where Q is moiety XII) are generated by reaction of 2-chlorobenzothiazoles (LV) with XLII according to the methods of R. Benassi (*J. Chem. Soc. Perkin Trans. II,* 1985, 1513).

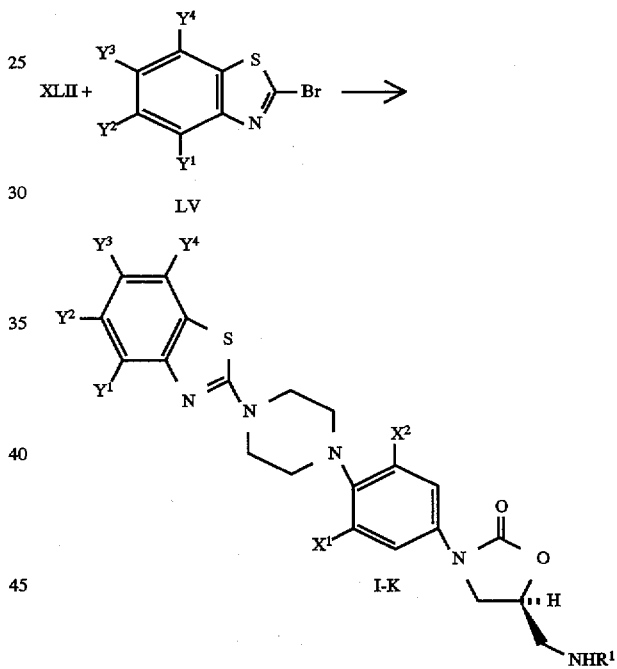

I-K

Thiazol-4-ones (I-L) of the present invention (structure I where Q is moiety XIII) are prepared by reaction of XLII with methyl thiocyanatoacetate (LVI) in keeping with the method of T. Zimmerman (*J. Prakt. Chem.* 1990, 332, 540).

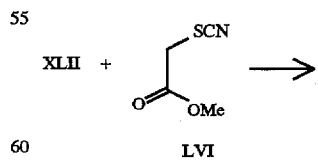

LVI

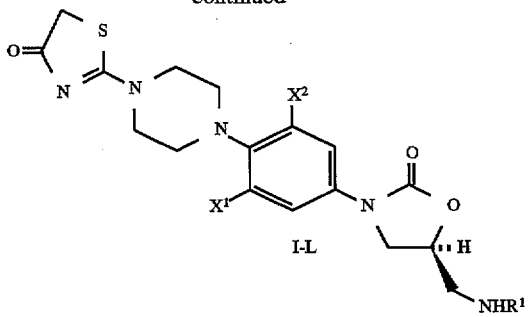

Thiazolediones (I-M) of the present invention (structure I where Q is moiety XIV) are made by reaction of XLII with triphenylphosphorylthiocyanate to first form the thiourea LVII according to the procedure of Y. Tamura (*Tetrahedron Lett.*, 1978, 20, 1753–1754). Thiourea LVII is then reacted with oxalyl chloride according to the procedures published by J. Goerdelen (*Chem. Ber.* 1966, 99, 3572) to afford the thiazolediones I-M.

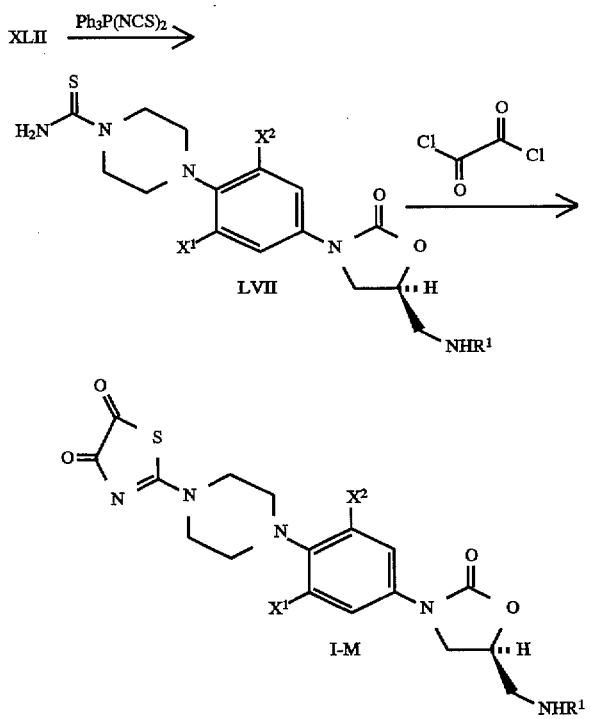

Thiazolines (I-N) of the present invention (structure I where Q is moiety XV) are made by reaction of XLII with 2-chloroethylisothiocyanates LVIII according to the procedures of R. E. Hackler (*Syn. Comm.*, 1975, 5, 143). The required 2-chloroethylisothiocyanates are commercially available or can be prepared by methods known in the literature.

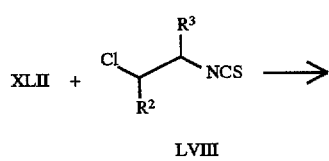

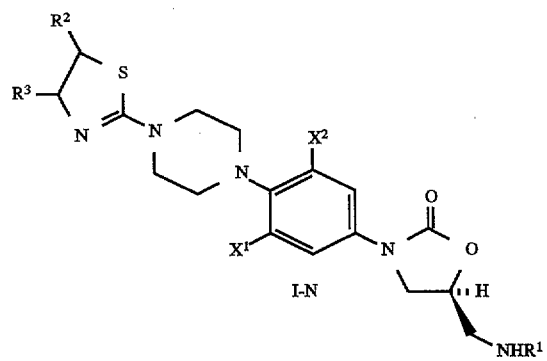

1,3,4-Thiadiazoles (I-O) of the present invention (structure I where Q is moiety XVI) are made by reaction of XLII with 2-bromo-1,3,4-thiadiazoles of structure LIX according to the procedures of I. Lalezari (*J. Pharm. Sci.*, 1975, 64 1250). The required 2-bromo-1,3,4-thiadiazoles can be prepared by methods known in the literature.

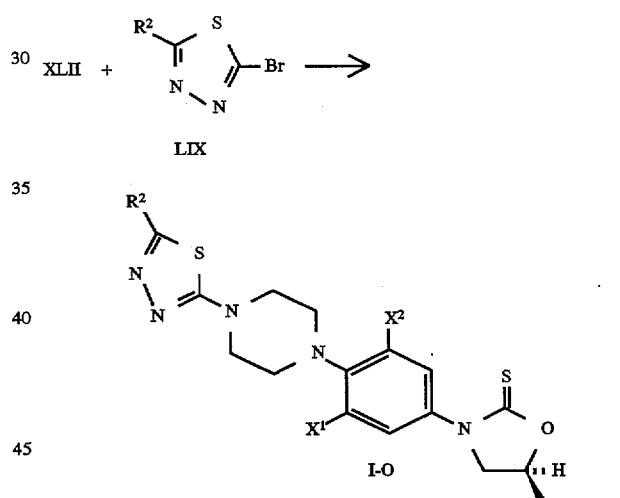

1,3,4-Thiadiazol-2-ones (I-P) of the present invention (structure I where Q is moiety XVII) are prepared by reaction of XLII with dithiosemicarbazides of structure LX to afford the intermediate thiosemicarbazides LXI which are then treated with phosgene. This pathway has been reported by K. Sasse (*Liebigs Ann. Chem.*, 1970, 735, 158).

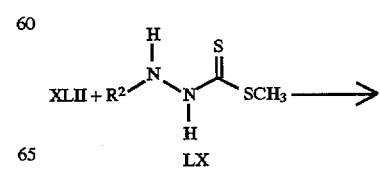

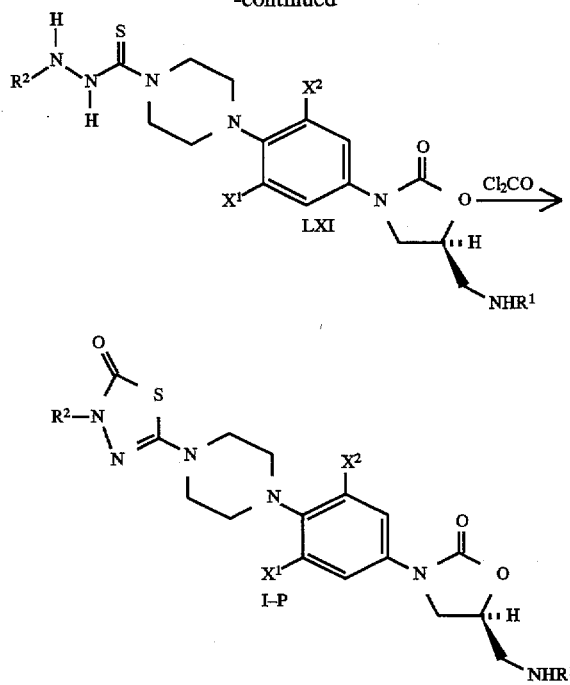

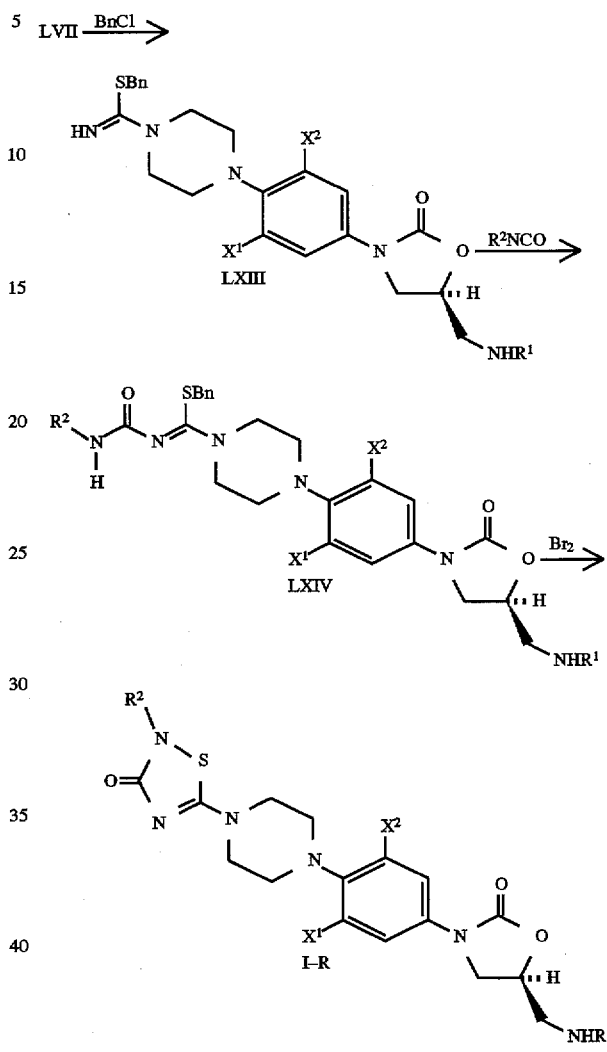

1,2,4-Thiadiazoles (I-Q) of the present invention (structure I where Q is structure XVIII) are made by reaction of XLII with 2-chloro-1,2,4-thiadiazoles LXII according to the procedures or E. F. Elslager (*J. Her. Chem.*, 1973, 10, 611). The required 2-chloro-1,2,4-thiadiazoles are commercially available or can be prepared by methods known in the literature.

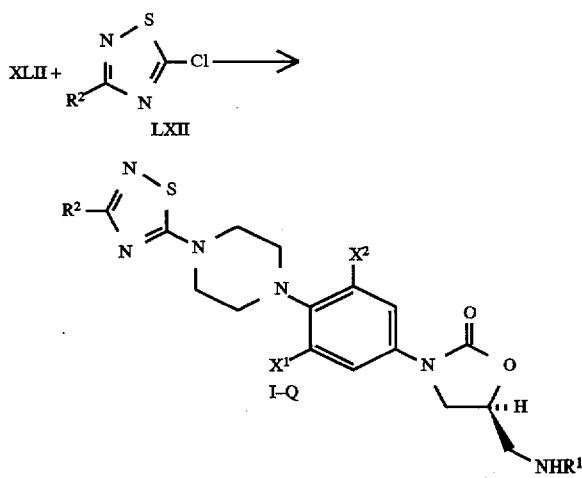

1,2,4-Thiadiazol-3-ones (I-R) of the present invention (structure I where Q is structure XIX) are made by a multistep reaction sequence reported by A. K. Pandey (*Synthesis*, 1982, 1068). In this sequence, the thiourea LVII (preparation described above) is alkylated with benzyl chloride to give the isothiourea LXIII. This isothiourea is then reacted with an isocyanate to give the intermediate LXIV. Finally LXIV is treated with bromine to produce the 1,2,4-thiadiazol-3-one I-R.

1,2,5-Thiadiazoles (I-S) of the present invention (structure I where Q is moiety XX) are made by reaction of XLII with 3,4-dialkoxy-1,2,5-thiadiazoles (LXV) according to the procedures of S. Karady (*Heterocycles*, 1981, 16, 1561-) and R. Y. Wen (*J. Org. Chem.*, 1975, 40, 2743). The required 3-methoxy-1,2,5-thiadiazoles are made by methods described in the same disclosures.

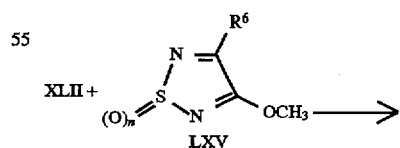

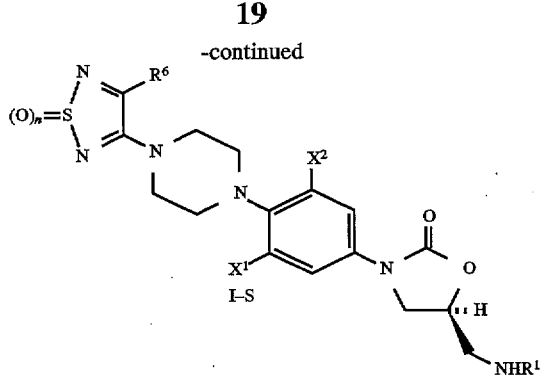

1,2,3,4-Thiatriazoles I-T of the present invention (structure I where Q is moiety XXI) are prepared by reaction of XLII with 5-chlorothiatriazole (LXVI) according to the methods of E. Lieber (*J. Org. Chem.*, 1961, 26, 1644).

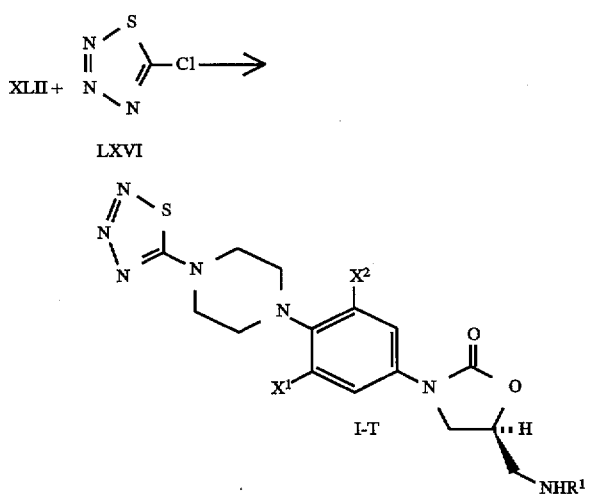

1,2,4-Dithiazolones I-U of the present invention (structure I where Q is moiety XXII) are obtained by reaction of the previously described thiourea LVII with chlorocarbonylsulfenyl chloride according to the procedures of J. Goerdeler (*Chem. Ber.* 1981, 114, 549).

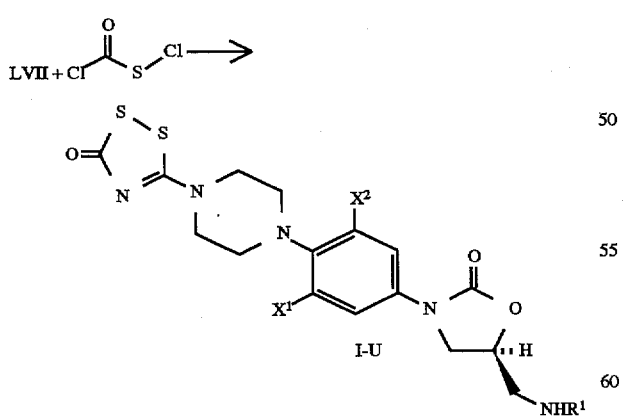

Imidazoles (I-V) of the present invention (structure I where Q is moiety XXIII) are made by reaction of the thiourea LVII (described above) with methyl iodide to afford the isothiourea LXVII and then further reaction with aminoacetaldehyde diethyl acetal according to the procedures of A. Dalkafouki (*Tetrahedron Lett.*, 1991, 32, 5325).

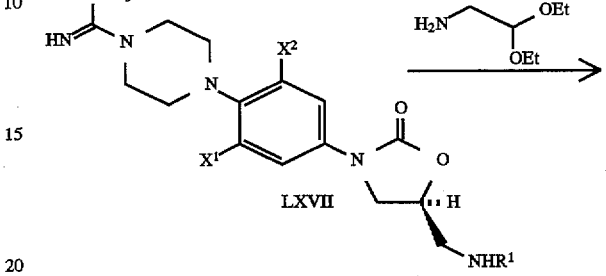

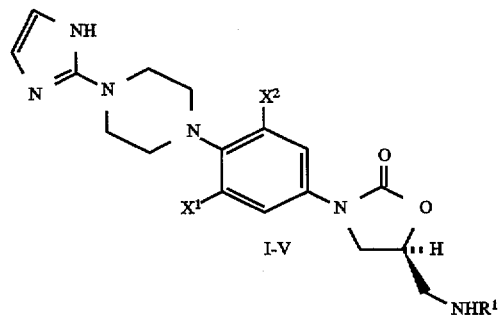

Benzimidazoles (I-W) of the present invention (structure I where Q is moiety XXIV) are made by reaction of XLII with 2-chlorobenzimidazoles LXVIII according to the procedures of I. R. Mandel (*J. Med. Chem.*, 1970, 13, 1043).

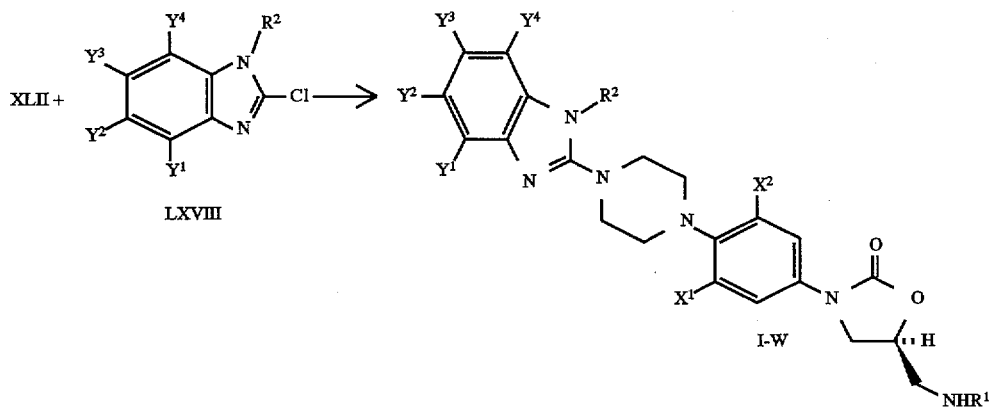

Imidazol-4-ones (I-X) of the present invention (structure I where Q is moiety XXV) are made by reaction of XLII with 2-methylthio-4-imidazolones (LXIX) according to the procedures of R. C. Gadwood, et al. (*J. Med. Chem.*, 1993, 36, 1480–1487). The required 2-methylthio-4-imidazolones can be made by procedures contained in this reference.

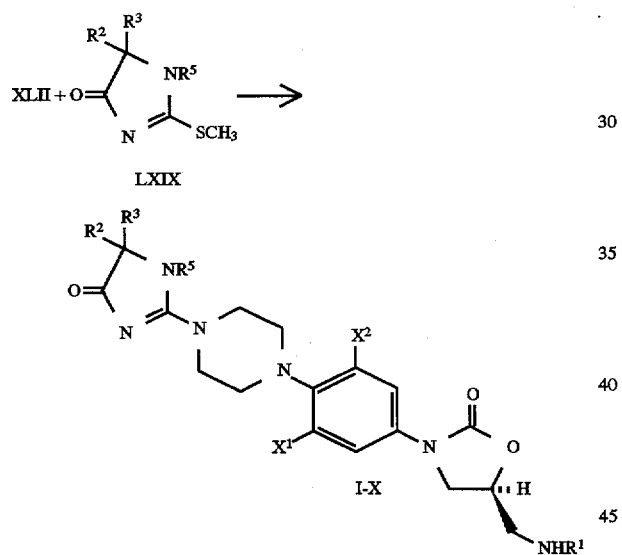

1,2,4-Triazoles (I-Y, I-Z, and I-AA) of the present invention (structure I where Q is structure XXVI, XXVII, or XXVIII) differ only in the type of substitution pattern found on the triazole. It is recognized that these triazoles are simply tautomers of one another when $R^3$ or $R^5$ is hydrogen (H). However, if $R^3$ or $R^5$ are alkyl or phenyl, then the triazoles I-Y, I-Z, and I-AA are unique, non-interconverting structures.

1,2,4-Triazoles of Type 1 (I-Y) of the present invention (structure I where Q is structure XXVI) are made by reaction of XLII with an isothiocyanate to afford the substituted thiourea LXX. Alkylation with methyl iodide gives the isothiourea LXXI, and reaction with hydrazides produces I-Y. These steps have been disclosed by J. P. Maffrand (*Eur. J. Med. Chem.* 1978, 13, 469).

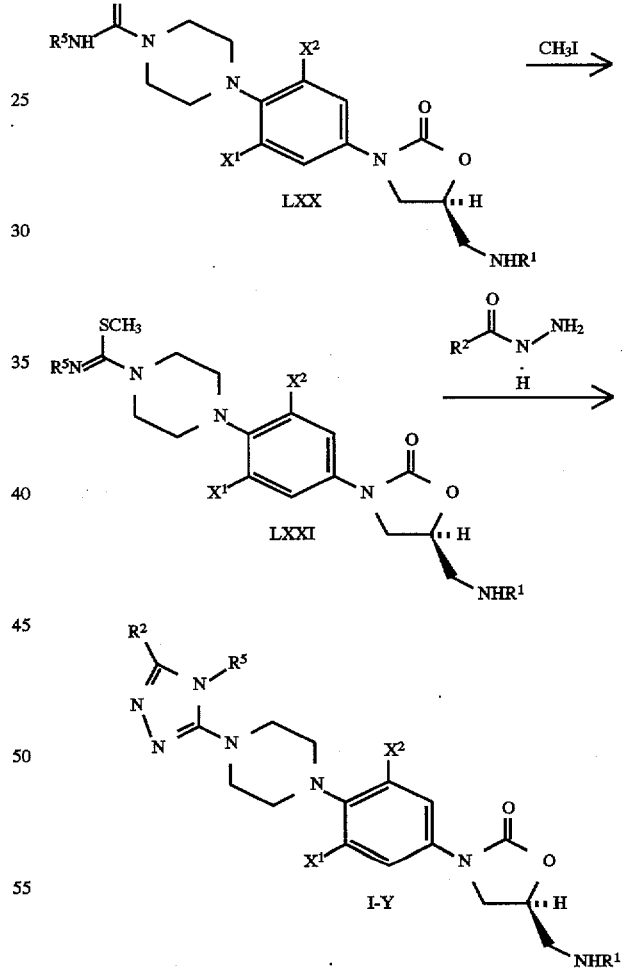

1,2,4-Triazoles of Type 2 (I-Z) of the present invention (structure I where Q is moiety XXVII) are made by reaction of 3-chloro-1,2,4-triazoles (LXXII) with XLII according to the procedures of J. L. Barascut. The required 3-chloro-1,2,4-triazoles are prepared by methods known in the literature.

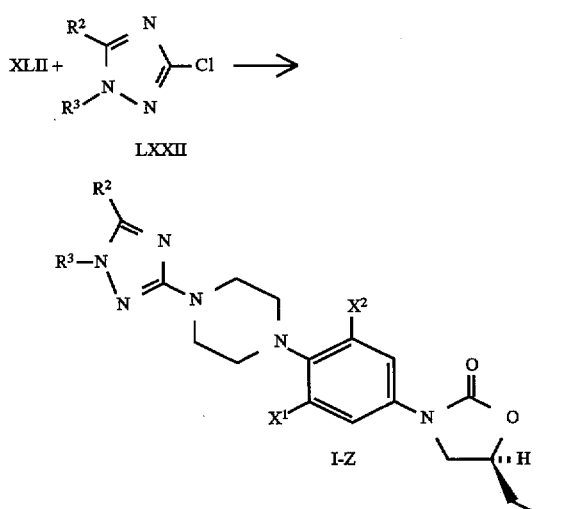

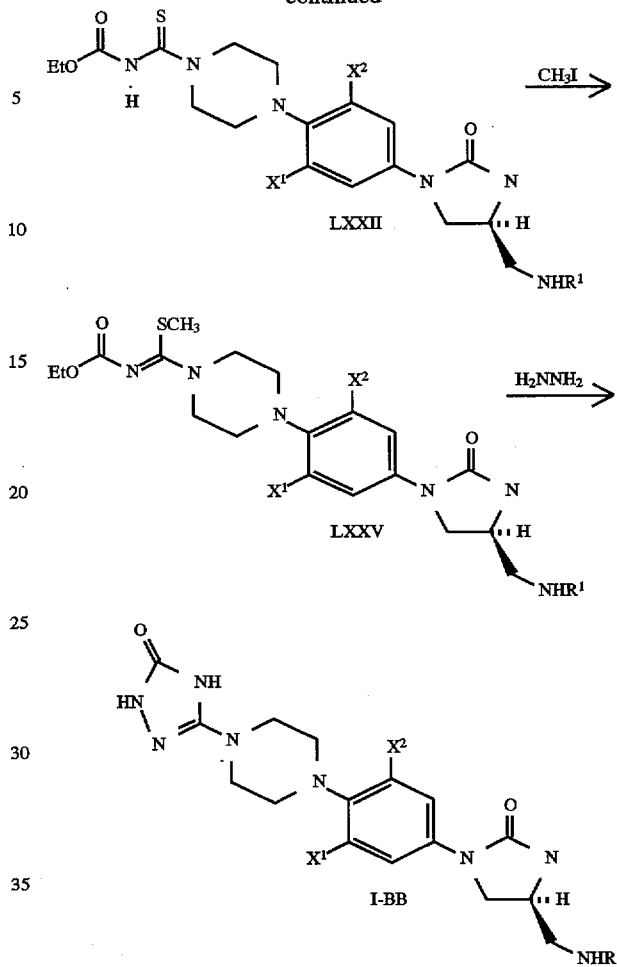

1,2,4-Triazoles of Type 3 (I-AA) of the present invention (structure I where Q is moiety XXVIII) are made by reaction of 3-bromo-1,2,4-triazoles (LXXIII) with XLII according to the procedures of J. L. Barascut (*Bull. Soc. Chim. Fr.*, 1975, 1649). The required 3-bromo-1,2,4-triazoles are prepared by methods also described by J. L. Barascut.

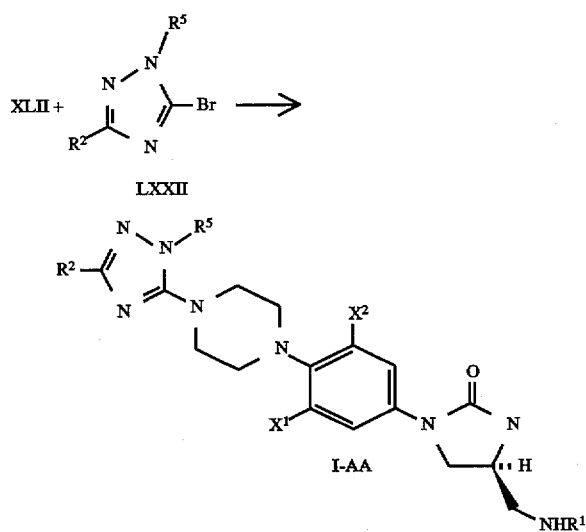

1,2,4-Triazolones (I-BB) of the present invention (structure I where Q is moiety XXIX) are made via a multistep sequence disclosed by P. R. Atkins (*J. Chem. Soc. Perkin I*, 1973, 2644). Thus, reaction of XLII with ethoxycarbonylisothiocyanate gives the thiourea LXXIV. Methylation produces the isothiourea LXXV and reaction with hydrazine leads to the desired 1,2,4-triazolones.

1,2,3-Triazoles (I-CC) of the present invention (structure I where Q is moiety XXX) are made by reaction of XLII with 1-methoxy-1,2,3-triazolium salts (LXXVI) according to the procedures of M. Begtrup (*Acta Chem. Scand. B*, 1986, 40, 262).

Tetrazoles (I-DD and I-EE) of the present invention (structure I where Q is moiety XXXI or XXXII) differ only in the type of substitution pattern found on the tetrazole ring. It is recognized that these tetrazoles are simply tautomers of one another when $R^2$ is hydrogen (H). However, if $R^2$ is alkyl or phenyl, then the tetrazoles I-DD and I-EE are unique, non-interconverting structures.

Tetrazoles of Type 1 (I-DD) of the present invention (structure I where Q is moiety XXXI) are made by reaction of 5-bromotetrazoles (LXXVII) with XLII according to the procedures of G. B. Barlin (*J. Chem. Soc. (B)*, 1967, 641). The required 5-bromotetrazoles are prepared by methods known in the literature.

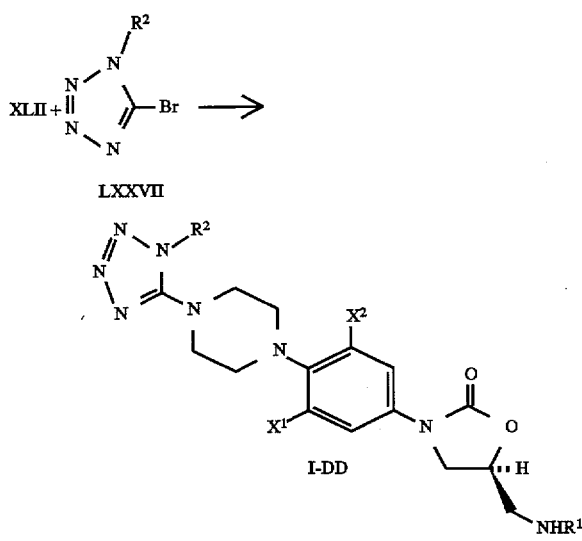

I-DD

Tetrazoles of Type 2 (I-EE) of the present invention (structure I where Q is moiety XXXII) are made by reaction of 5-bromotetrazoles (LXXVIII) with XLII. These methods have been reported by G. B. Barlin (*J. Chem. Soc. (B)*, 1967, 641).

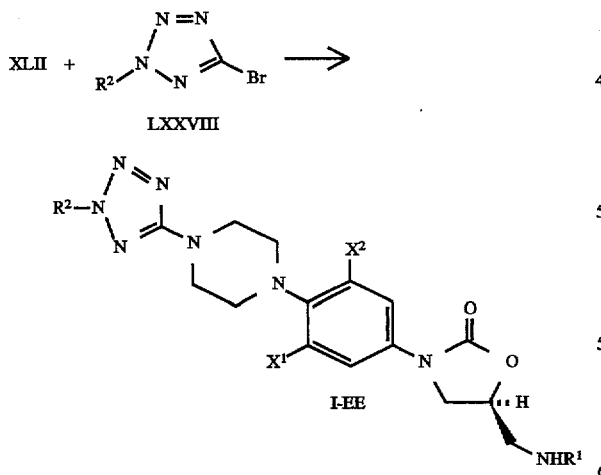

I-EE

Isoindol-7-ones (I-FF) of the present invention (structure I where Q is moiety XXXIII) are prepared by reaction of 2-aminoisoindol-7-ones (LXXIX) with XLII according to the procedures disclosed by L. L Spiessens (*Bull Soc. Chim. Belg.*, 1983, 92, 965). The required 2-aminoisoindol-7-ones are prepared by procedures outlined in the same publication.

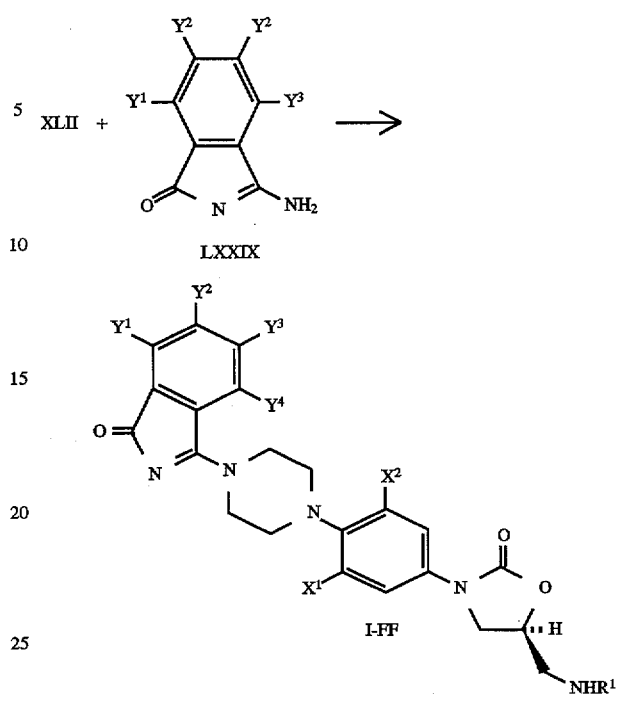

I-FF

Pyrazol-3-ones (I-GG) of the present invention (structure I where Q is moiety XXXIV) are prepared by the stepwise procedure outlined by H. J. Gais (*Helv. Chim. Acta*, 1969, 52, 2641). Reaction of XLII with methyl propiolate affords the enamine LXXX. Bromination and dehydrobromination leads to the ynamine LXXXI. Finally reaction with hydrazine gives the pyrazol-3-ones.

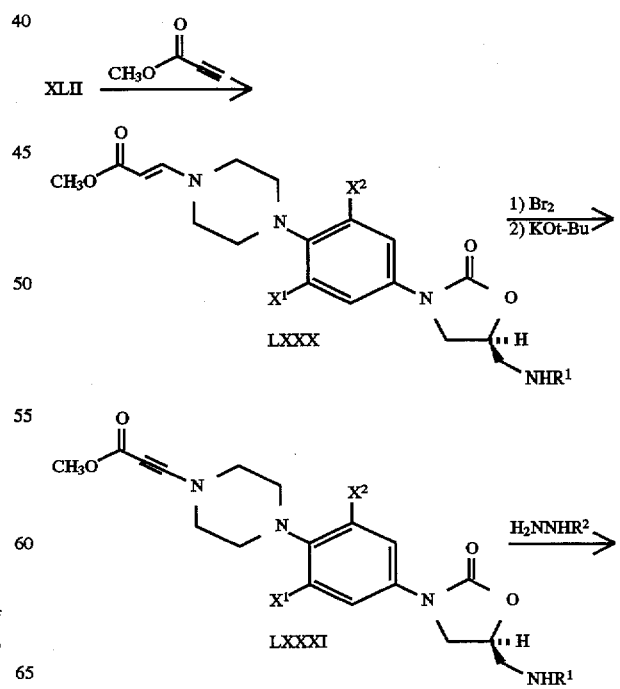

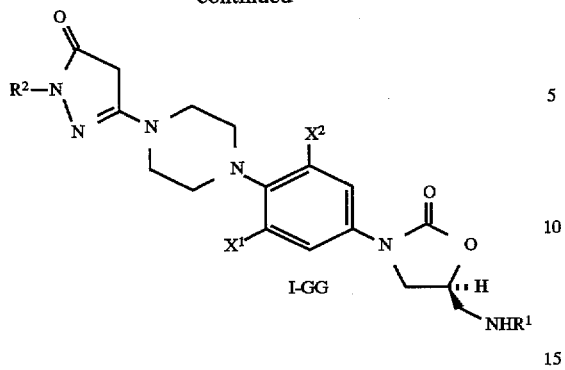

Pyrazolines (I-HH) of the present invention (structure I where Q is moiety XXXV) are made by following procedures described by J. Elguero (*Bull. Soc. Chim. Fr.,* 1969, 1683). Thus XLII is reacted with 3-bromopyrazolines LXXXII to afford the pyrazolines.

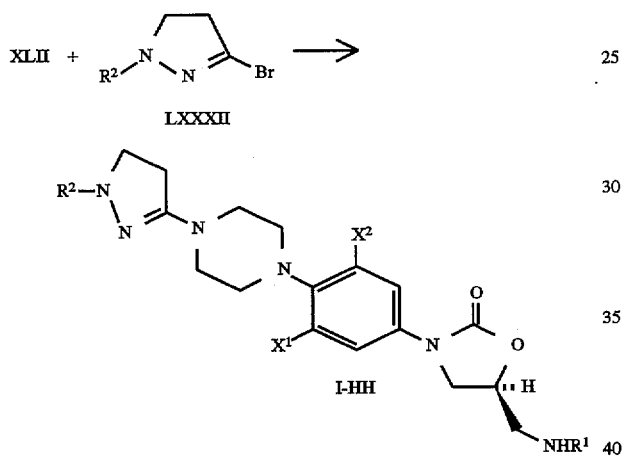

Pyrazoles I-II of the present invention (structure I where Q is moiety XXXVI) are made by a multistep procedure disclosed by I. G. Ostromuv (*J. Org. Chem., USSR,* 1987, 23, 1467). Reaction of XLII with an alkynone affords the enamine LXXXIII. Bromination and dehydrobromination gives the ynamine LXXXIV. Finally, reaction with hydrazines produces the pyrazoles I-II.

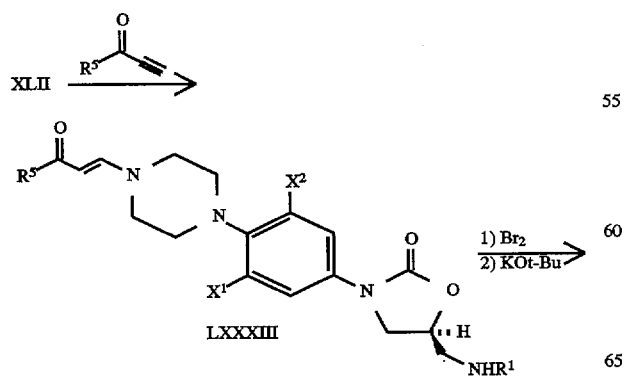

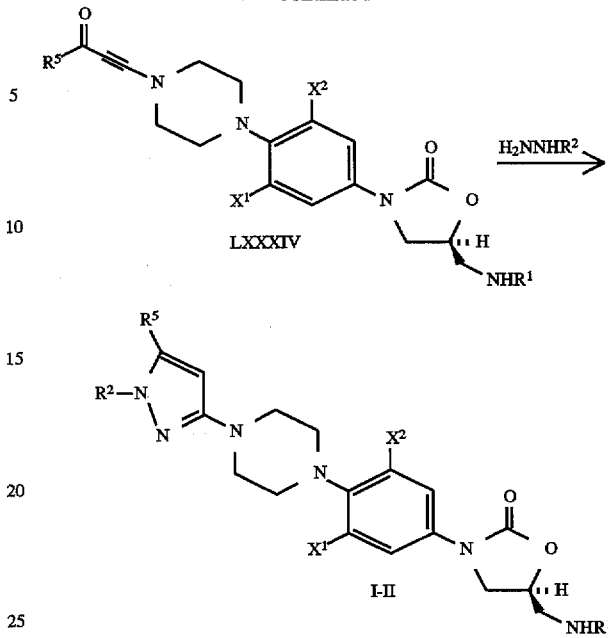

Indazoles (I-JJ) of the present invention (structure I where Q is moiety XXXVII) are prepared by reaction of XLII with 2-nitroindazoles (LXXXV) according to the methods of U. Wrzeciono (*Pharmazie,* 1985, 40, 105).

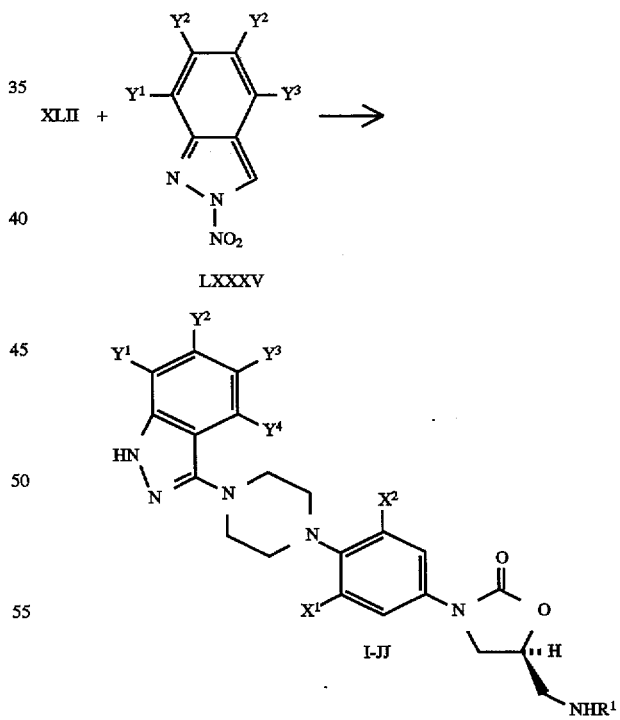

Benzoisothiazoles (I-KK) of the present invention (structure I where Q is moiety XXXVIII and n is 0) are synthesized by the reaction of XLII with 3-chlorobenzoisothiazoles (LXXXVI) according to the procedure of F. Becke (*J. Liebigs Ann. Chem.* 1969, 729, 146). Conversion to the benzisothiazoles (where n is 1 or 2) is carried out by oxidation according to the methods of H. B öshagen (Chem. Ber., 1970, 103, 3166).

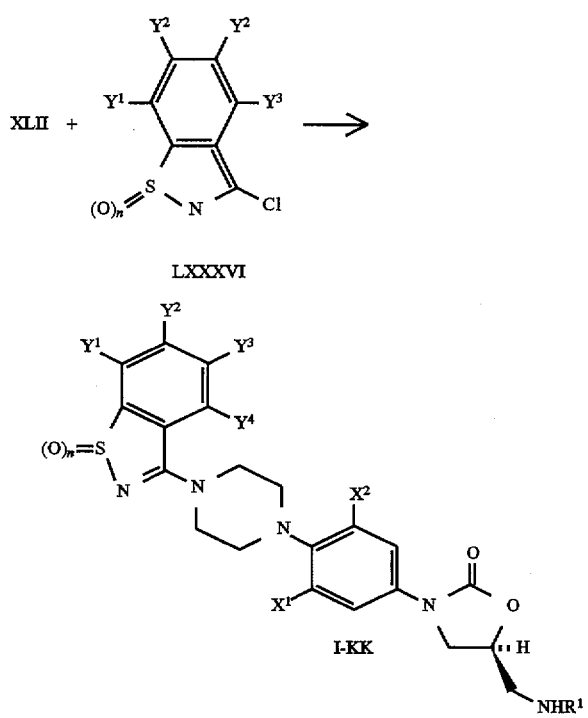

Isoxazoles (I-LL) of the present invention (structure I where Q is moiety XXXIX) are made by reaction of XLII with 3-chloro-2-methylisoxazole salts (LXXXVII) according to the procedure of S. Sugai (Chem. Pharm. Bull., 1984, 32, 530). The required 3-chloro-2-methylisoxazole salts are made by procedures disclosed in the above reference.

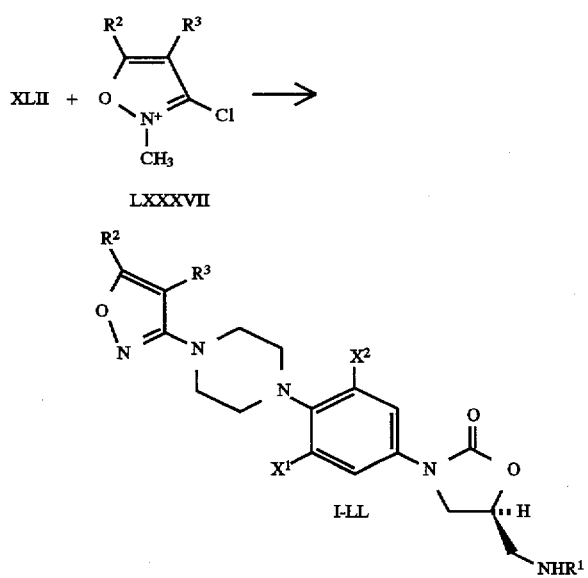

1,2,3-Oxathiazolidines (I-MM) of the present invention (structure I where Q is moiety XL) are made by reaction of XLII with 4-chloro-1,2,3-oxathiazolidines (LXXXVIII) according to the procedures of V. V. Dovlatyan (Arm. Khim. Zh., 1975, 28, 233; Chem. Abstracts 83: 58725v). The required 4-chloro-1,2,3-oxathiazolidines are made according to procedures disclosed in the above reference.

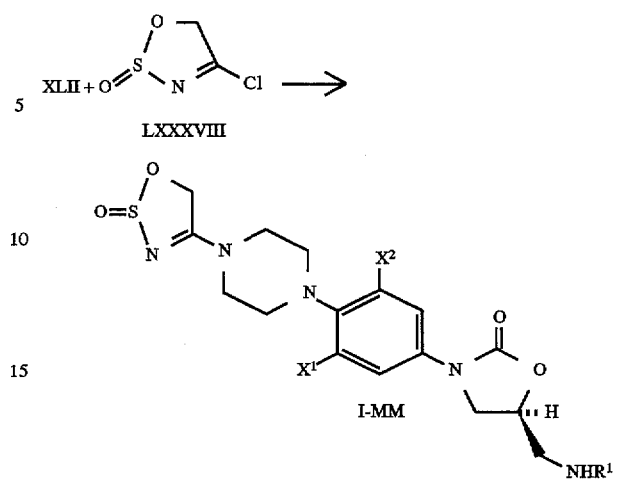

Benxisoxazoles (I-NN) of the present invention (structure I where Q is moiety XLI) are prepared by reaction of XLII with 3-chlorobenzisoxazoles (LXXXIX) according to the procedures of H. Böshagen (Chem. Ber., 1967, 100, 3326).

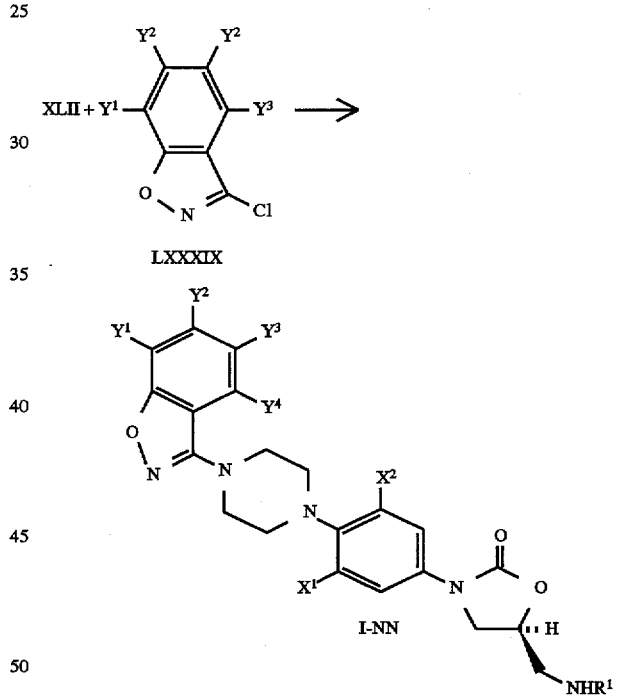

The compounds of Formula I are useful for treatment of microbial infections in humans and other warm blooded animals, under both parenteral, topical and oral administration.

The pharmaceutical compositions of this invention may be prepared by combining the compounds of Formula I of this invention with a solid or liquid pharmaceutically acceptable carrier and, optionally, with pharmaceutically acceptable adjuvants and excipients employing standard and conventional techniques. Solid form compositions include powders, tablets, dispersible granules, capsules, cachets and suppositories. A solid carrier can be at least one substance which may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like. Liquid form compositions include solutions, suspensions and emulsions. For example, there may be provided solutions of the compounds of this invention dissolved in water and water-propylene glycol and water-polyethylene glycol systems, optionally containing suitable conventional coloring agents, flavoring agents, stabilizers and thickening agents.

Preferably, the pharmaceutical composition is provided employing conventional techniques in unit dosage form containing effective or appropriate amounts of the active component, that is, the compound of Formula I according to this invention.

The quantity of active component, that is the compound of Formula I according to this invention, in the pharmaceutical composition and unit dosage form thereof may be varied or adjusted widely depending upon the particular application, the potency of the particular compound, the desired concentration. Generally, the quantity of active component will range between 0.5% to 90% by weight of the composition.

In therapeutic use for treating, or combatting, bacterial infections in warm-blooded animals, the compounds or pharmaceutical compositions thereof will be administered orally and/or parenterally at a dosage to obtain and maintain a concentration, that is, an amount, or blood-level of active component in the animal undergoing treatment which will be antibacterially effective. Generally, such antibacterially effective amount of dosage of active component will be in the range of about 0.1 to about 100, more preferably about 3.0 to about 50 mg/kg of body weight/day. It is to be understood that the dosages may vary depending upon the requirements of the patient, the severity of the bacterial infection being treated, and the particular compound being used. Also, it is to be understood that the initial dosage administered may be increased beyond the above upper level in order to rapidly achieve the desired blood-level or the initial dosage may be smaller than the optimum and the daily dosage may be progressively increased during the course of treatment depending on the particular situation. If desired, the daily dose may also be divided into multiple doses for administration, e.g., two to four times per day.

The compounds of Formula I according to this invention are administered parenterally, i.e., by injection, for example, by intravenous injection or by other parenteral routes of administration. Pharmaceutical compositions for parenteral administration will generally contain a pharmaceutically acceptable amount of the compound according to Formula I as a soluble salt (acid addition salt or base salt) dissolved in a pharmaceutically acceptable liquid carrier such as, for example, water-for-injection and a buffer to provide a suitably buffered isotonic solution, for example, having a pH of about 3-7. Suitable buffering agents include, for example, trisodium orthophosphate, sodium bicarbonate, sodium citrate, N-methylglucamine, L(+)-lysine and L(+)-arginine to name but a few representative buffering agents. The compound according to Formula I generally will be dissolved in the carrier in an amount sufficient to provide a pharmaceutically acceptable injectable concentration in the range of about 1 mg/ml to about 400 mg/ml of solution. The resulting liquid pharmaceutical composition will be administered so as to obtain the above-mentioned antibacterially effective amount of dosage. The compounds of Formula I according to this invention, due to their aqueous solubility, are advantageously administered orally in solid and liquid dosage forms.

Representative compounds of this invention are the following:

a) (S)—N—[[3-[3-Fluoro-4-[4-(2-oxazolyl)-1-piperazinyl]phenyl]-2-oxo-5-oxazolidinyl]methyl] acetamide (I-A);

b) (S)—N—[[3-[3-Fluoro-4-[4-(4-oxo-2-oxazolinyl)-1-piperazinyl]phenyl]-2-oxo-5-oxazolidinyl]methyl] acetamide (I-B);

c) (S)—N—[[3-[3-Fluoro-4-[4-(4,5-dihydro-2-oxazolyl)-1-piperazinyl]phenyl]-2-oxo-5-oxazolidinyl]methyl] acetamide (I-C);

d) (S)—N—[[3-[4-[4-(2-Benzoxazolyl)-1-piperazinyl]-3-fluorophenyl]-2-oxo-5-oxazolidinyl]methyl]acetamide (I-D);

e) (S)—N—[[3-[3-Fluoro-4-[4-(5-nitrobenzoxazol-2-yl)-1-piperazinyl]phenyl]-2-oxo-5-oxazolidinyl]methyl] acetamide (I-D);

f) (S)—N—[[3-[3-Fluoro-4-[4-(5-fluorobenzoxazol-2-yl)-1-piperazinyl]phenyl]-2-oxo-5-oxazolidinyl]methyl] acetamide (I-D);

g) (S)—N—[[3-[3-Fluoro-4-[4-(6-fluorobenzoxazol-2-yl)-1-piperazinyl]phenyl]-2-oxo-5-oxazolidinyl]methyl] acetamide (I-D);

h) (S)—N—[[3-[3-Fluoro-4-[4-(7-fluorobenzoxazol-2-yl)-1-piperazinyl]phenyl]-2-oxo-5-oxazolidinyl]methyl] acetamide (I-D);

i) (S)—N—[[3-[3-Fluoro-4-[4-(6,7-difluorobenzoxazol-2-yl)-1-piperazinyl]phenyl]-2-oxo-5-oxazolidinyl]methyl] acetamide (I-D);

j) (S)—N—[[3-[3-Fluoro-4-[4-(1,3,4-oxadiazol-2-yl)-1-piperazinyl]phenyl]-2-oxo-5-oxazolidinyl]methyl] acetamide (I-E);

k) (S)—N—[[3-[3-Fluoro-4-[4-(1,2,4-oxadiazol-5-yl)-1-piperazinyl]phenyl]-2-oxo-5-oxazolidinyl]methyl] acetamide (I-F);

l) (S)—N—[[3-[3-Fluoro-4-[4-(1,2,4-oxadiazol-3-yl)-1-piperazinyl]phenyl]-2-oxo-5-oxazolidinyl]methyl] acetamide (I-G);

m) (S)—N—[[3-[3-Fluoro-4-[4-(5-oxo-1,2,4-oxadiazol-3-yl)-1-piperazinyl]phenyl]-2-oxo-5-oxazolidinyl]methyl] acetamide (I-H);

n) (S)—N—[[3-[3-Fluoro-4-[4-(2-oxo-1,3,4-oxathiazol-5-yl)-1-piperazinyl]phenyl]-2-oxo-5-oxazolidinyl]methyl] acetamide (I-I);

o) (S)—N—[[3-[3-Fluoro-4-[4-(2-thiazolyl)-1-piperazinyl]phenyl]-2-oxo-5-oxazolidinyl]methyl] acetamide (I-J);

p) (S)—N—[[3-[3-Fluoro-4-[4-(5-nitrothiazol-2-yl)-1-piperazinyl]phenyl]-2-oxo-5-oxazolidinyl]methyl] acetamide (I-J);

q) (S)—N—[[3-[4-[4-(2-Benzothiazolyl)-1-piperazinyl]-3-fluorophenyl]-2-oxo-5-oxazolidinyl]methyl]acetamide (I-K);

r) (S)—N—[[3-[3-Fluoro-4-[4-(6-nitrobenzothiazol-2-yl)-1-piperazinyl]phenyl]-2-oxo-5-oxazolidinyl]methyl] acetamide (I-K);

s) (S)—N—[[3-[3-Fluoro-4-[4-(4-oxo-2-thiazolinyl)-1-piperazinyl]phenyl]-2-oxo-5-oxazolidinyl]methyl] acetamide (I-L);

t) (S)—N—[[3-[4-[4-(4,5-Dioxo-2-thiazolinyl)-1-piperazinyl]-3-fluorophenyl]-2-oxo-5-oxazolidinyl]methyl] acetamide (I-M);

u) (S)—N—[[3-[4-[4-(4,5-Dihydro-2-thiazolyl)-1-piperazinyl]-3-fluorophenyl]-2-oxo-5-oxazolidinyl]methyl] acetamide (I-N);

v) (S)—N—[[3-[3-Fluoro-4-[4-(1,3,4-thiadiazol-2-yl)-1-piperazinyl]phenyl]-2-oxo-5-oxazolidinyl]methyl] acetamide (I-O);

w) (S)—N—[[3-[3-Fluoro-4-[4-(5-oxo-1,3,4-thiadiazol-2-yl)-1-piperazinyl]phenyl]-2-oxo-5-oxazolidinyl]methyl] acetamide (I-P);

x) (S)—N—[[3-[3-Fluoro-4-[4-(1,2,4-thiadiazol-5-yl)-1-piperazinyl]phenyl]-2-oxo-5-oxazolidinyl]methyl] acetamide (I-Q);

y) (S)—N—[[3-[3-Fluoro-4-[4-(3-oxo-1,2,4-thiadiazol-5-yl)-1-piperazinyl]phenyl]-2-oxo-5-oxazolidinyl]methyl] acetamide (I-R);

z) (S)—N—[[3-[3-Fluoro-4-[4-(1,2,5-thiadiazol-3-yl)-1-piperazinyl]phenyl]-2-oxo-5-oxazolidinyl]methyl] acetamide (I-S);

aa) (S)—N—[[3-[3-Fluoro-4-[4-(1,2,3,4-thiatriazol-5-yl)-1-piperazinyl]phenyl]-2-oxo-5-oxazolidinyl]methyl] acetamide (I-T);

bb) (S)—N—[[3-[3-Fluoro-4-[4-(3-oxo-1,2,4-dithiazol-5-yl)-1-piperazinyl]phenyl]-2-oxo-5-oxazolidinyl]methyl] acetamide (I-U);

cc) (S)—N—[[3-[3-Fluoro-4-[4-(imidazol-2-yl)-1-piperazinyl]phenyl]-2-oxo-5-oxazolidinyl]methyl] acetamide (I-V);

dd) (S)—N—[[3-[4-[4-(2-Benzimidazolyl)-1-piperazinyl]-3-fluorophenyl]-2-oxo-5-oxazolidinyl]methyl] acetamide (I-W);

ee) (S)—N—[[3-[3-Fluoro-4-[4-(4-oxo-2-imidazolinyl)-1-piperazinyl]phenyl]-2-oxo-5-oxazolidinyl]methyl] acetamide (I-X);

ff) (S)—N—[[3-[3-Fluoro-4-[4-(1,2,4-triazol-3-yl)-1-piperazinyl]phenyl]-2-oxo-5-oxazolidinyl]methyl] acetamide (I-Y, I-Z, and I-AA);

gg) (S)—N—[[3-[3-Fluoro-4-[4-(3-oxo-1,2,4-triazol-5-yl)-1-piperazinyl]phenyl]-2-oxo-5-oxazolidinyl]methyl] acetamide (I-BB);

hh) (S)—N—[[3-[3-Fluoro-4-[4-(1,2,3-triazol-5-yl)-1-piperazinyl]phenyl]-2-oxo-5-oxazolidinyl]methyl] acetamide (I-CC);

ii) (S)—N—[[3-[4-[3-Fluoro-4-[(1-phenyl-5-tetrazolyl)-1-piperazinyl]phenyl]-2-oxo-5-oxazolidinyl]methyl] acetamide (I-DD);

jj) (S)—N—[[3-[4-[3-Fluoro-4-[(2-methyl-5-tetrazolyl)-1-piperazinyl]phenyl]-2-oxo-5-oxazolidinyl]methyl] acetamide (I-EE);

kk) (S)—N—[[3-[4-[3-Fluoro-4-[(3-oxo-7-isoindolyl)-1-piperazinyl]phenyl]-2-oxo-5-oxazolidinyl]methyl] acetamide (I-FF);

ll) (S)—N—[[3-[4-[3-Fluoro-4-[(3-oxo-5-pyrazolinyl)-1-piperazinyl]phenyl]-2-oxo-5-oxazolidinyl]methyl] acetamide (I-GG);

mm) (S)—N—[[3-[4-[3-Fluoro-4-[(3,4-dihydropyrazol-5-yl)-1-piperazinyl]phenyl]-2-oxo-5-oxazolidinyl]methyl] acetamide (I-HH);

nn) (S)—N—[[3-[4-[3-Fluoro-4-[(3-pyrazolyl)-1-piperazinyl]phenyl]-2-oxo-5-oxazolidinyl]methyl] acetamide (I-II);

oo) (S)—N—[[3-[4-[3-Fluoro-4-[(3-indazolyl)-1-piperazinyl]phenyl]-2-oxo-5-oxazolidinyl]methyl] acetamide (I-JJ);

pp) (S)—N—[[3-[4-[4-[(3-Benzoisothiazolyl)-1-piperazinyl]-3-fluorophenyl]-2-oxo-5-oxazolidinyl]methyl] acetamide (I-KK);

qq) (S)—N—[[3-[3-Fluoro-4-[4-(isoxazol-3-yl)-1-piperazinyl]phenyl]-2-oxo-5-oxazolidinyl]methyl] acetamide (I-LL);

rr) (S)—N—[[3-[3-Fluoro-4-[4-(1,2,3-oxathiazol-5-yl)-1-piperazinyl]phenyl]-2-oxo-5-oxazolidinyl]methyl] acetamide, S-oxide (I-MM);

ss) (S)—N—[[3-[4-[4-[(7-Benzisoxazolyl)-1-piperazinyl]-3-fluorophenyl]-2-oxo-5-oxazolidinyl]methyl] acetamide (I-NN);

tt) (S)—N—[[3-[3-Fluoro-4-[4-(5-methyl-1,3,4-thiadiazol-2-yl)-1-piperazinyl]phenyl]-2-oxo-5-oxazolidinyl]methyl]acetamide;

uu) (S)—N—[[3-[4-[4-(5-Amino-1,3,4-thiadiazol-2-yl)-3-fluoro-1-piperazinyl]phenyl]-2-oxo-5-oxazolidinyl]methyl]acetamide;

vv) (S)—N—[[3-[4-[4-(5-Ethoxycarbonyl-1,3,4-thiadiazol-2-yl)-3-fluoro-1-piperazinyl]phenyl]-2-oxo-5-oxazolidinyl]methyl]acetamide;

ww) (S)—N—[[3-[3-Fluoro-4-[4-(5-trifluoromethyl-1,3,4-thiadiazol-2-yl)-1-piperazinyl]phenyl]-2-oxo-5-oxazolidinyl]methyl]acetamide;

xx) (S)—N—[[3-[4-[4-(5-Aminocarbonyl-1,3,4-thiadiazol-2-yl)-3-fluoro-1-piperazinyl]phenyl]-2-oxo-5-oxazolidinyl]methyl]acetamide;

yy) (S)—N—[[3-[4-[4-(5-Cyano-1,3,4-thiadiazol-2-yl)-3-fluoro-1-piperazinyl]phenyl]-2-oxo-5-oxazolidinyl]methyl]acetamide;

zz) (S)—N—[[3-[3-Fluoro-4-[4-(5-methylthio-1,3,4-thiadiazol-2-yl)-1-piperazinyl]phenyl]-2-oxo-5-oxazolidinyl]methyl]acetamide;

aaa) (S)—N—[[3-[3-Fluoro-4-[4-(3-methyl-1,2,4-thiadiazol-5-yl)-1-piperazinyl]phenyl]-2-oxo-5-oxazolidinyl]methyl]acetamide;

bbb) (S)—N—[[3-[3-Fluoro-4-[4-(2-phenyl-3-oxo-1,2,4-thiadiazol-5-yl)-1-piperazinyl]phenyl]-2-oxo-5-oxazolidinyl]methyl]acetamide;

ccc) (S)—N—[[3-[3-Fluoro-4-[4-(5-methyl-1,3,4-oxadiazol-2-yl)-1-piperazinyl]phenyl]-2-oxo-5-oxazolidinyl]methyl]acetamide;

ddd) (S)—N—[[3-[4-[4-(5-Ethyl-1,3,4-thiadiazol-2-yl)-1-piperazinyl]-3-fluorophenyl]-2-oxo-5-oxazolidinyl]methyl]acetamide;

eee) (S)—N—[[3-[3-Fluoro-4-[4-(5-propyl-1,3,4-thiadiazol-2-yl)-1-piperazinyl]-phenyl]-2-oxo-5-oxazolidinyl]methyl]acetamide;

fff) (S)—N—[[3-[3-Fluoro-4-[4-(5-(1-methyl)ethyl-1,3,4-thiadiazol-2-yl)-1-piperazinyl]-phenyl]-2-oxo-5-oxazolidinyl]methyl]acetamide; or ggg) (S)—N—[[3-[4-[4-(5-Cyclopropyl-1,3,4-thiadiazol-2-yl)-1-piperazinyl]-3-fluoro-phenyl]-2-oxo-5-oxazolidinyl]methyl]acetamide.

The oxazolidinone antibacterial agents of this invention have useful activity against a variety of organisms. The in vitro activity of compounds of this invention can be assessed by standard testing procedures such as the determination of minimum inhibitory concentration (MIC) by agar dilution as described in "Methods for Dilution Antimicrobial Susceptibility Tests for Bacteria That Grow Aerobically" (MFT) published January 1983 by the National Committee for Clinical Laboratory Standards, 771 East Lancaster Avenue, Villanova, Pa. 19084, USA. The activity of selected compounds of this invention against *Staphylococcus aureus* and *Streptococcus pneumoniae* are shown in Table 1.

Antimicrobial activity was tested in vivo using the Murine Assay procedure. Groups of female mice (six mice of 18–20 grams each) were injected intraperitoneally with bacteria which were thawed just prior to use and suspended in brain heart infusion with 4% brewers yeast *S. aureus* UC® 9213 or brain heart infusion (Streptococcus species). Antibiotic treatment at six dose levels per drug was administered one hour and five hours after infection by either oral intubation or subcutaneous ("subcut.") routes. Survival was observed daily for six days. $ED_{50}$ values based on mortality ratios were calculated using probit analysis. The subject compounds were compared against a well-known antimicrobial (Vancomycin) as a control. The data are shown in Table 1.

TABLE 1

In Vitro Activity of Examples Against Selected Gram-Positive Bacteria MIC (μg/mL)*

| Example No. | *S. aureus* UC ® 9213 | *E. Faecalis* UC ® 9217 |
|---|---|---|
| 1 | 4 | 2 |
| 2 | 2 | 2 |
| 3 | 2 | 2 |
| 4 | 1 | 1 |
| 5 | 2 | 1 |
| 6 | 0.5 | 0.5 |
| 7 | 4 | 4 |
| 8 | 2 | 1 |
| 9 | 1 | 1 |
| 10 | 2 | 2 |
| 11 | 2 | 1 |
| 12 | 32 | 4 |
| 13 | 4 | 4 |
| 14 | 4 | 2 |
| 15 | 2 | 1 |
| 16 | 1 | 1 |
| 17 | 0.5 | 1 |
| 18 | 2 | 2 |
| 19 | 4 | 2 |
| 20 | 4 | 2 |
| 24 | 1 | 1 |
| 25 | 2 | 1 |
| 26 | 8 | 4 |
| 27 | 4 | 4 |
| XLII | >64 | 32 |
| Vancomycin | 1 | 4 |

*Minimum inhibitory concentration: lowest concentration of drug (μg/mL) that inhibits visible growth of the organism.

EXAMPLE 1

(S)—N—[[3-[4-[4-(2-Benzothiazolyl)-1-piperazinyl]
-3-fluorophenyl]-2-oxo-5-oxazolidinyl]methyl]
acetamide

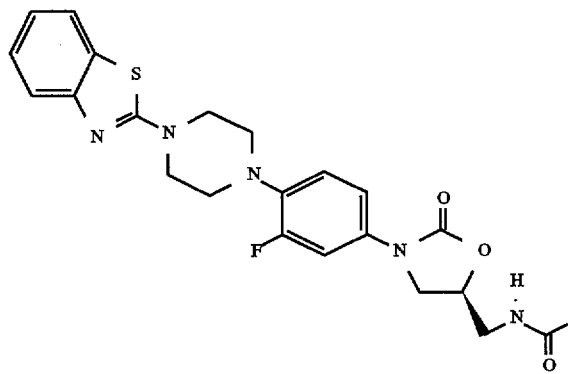

The starting material XLII (where $X^1$ is fluorine (F), $X^2$ is hydrogen (H), and $R^1$ is acetyl ($COCH_3$)) (350 mg, 1.04 mmol) is dissolved into 6 mL of DMSO. The solution is treated with dibasic potassium phosphate (362 mg, 2.08 mmol) and 2-chlorobenzothiazole (194 mg, 1.14 mmol). The mixture is heated to 90° C. under $N_2$. After 3 hours TLC analysis shows starting material is consumed. The mixture is cooled and poured into a separatory funnel along with $CH_2Cl_2$ and $H_2O$. The mixture is shaken and the organic phase is separated and washed with additional $H_2O$. The organic phase is dried over anhydrous $Na_2SO_4$. The solution is filtered and concentrated to give a solid that is triturated with $CH_2Cl_2/Et_2O$. The solids are filtered, washed with additional $Et_2O$ and dried in vacuo to give 341 mg of the title compound. MP: 239°–240° C.

EXAMPLE 2

(S)—N—[[3-[3-Fluoro-4-[4-(5-nitrothiazol-2-yl)-1-
piperazinyl]phenyl]-2-oxo-5-oxazolidinyl]methyl]
acetamide

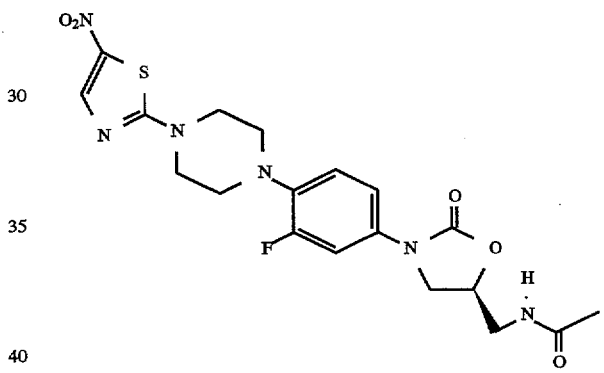

The starting material XLII (where $X^1$ is fluorine (F), $X^2$ is hydrogen (H), and $R^1$ is acetyl ($COCH_3$)) (400 mg, 1.19 mmol) is dissolved into 7 mL of DMSO. The solution is treated with $K_2HPO_4$ (414 mg, 2.38 mmol) and 2-bromo-5-nitrothiazole (286 mg, 1.37 mmol). The mixture is stirred at room temperature under $N_2$. After 16 hours TLC shows starting material is consumed. The mixture is poured into a separatory funnel along with $CH_2Cl_2$. The mixture is washed with $H_2O$ and brine, and the organic phase is separated and dried over anhydrous $Na_2SO_4$. Filtration and concentration of the organic phase gives an orange oil. This material is filtered through a plug of silica gel eluting with 3% MeOH/$CHCl_3$. The filtrate is concentrated to give an oil that is treated with MeOH. The resulting slurry is diluted with $Et_2O$ and the solids are filtered and washed with $Et_2O$. The solids are dried in vacuo to give 391 mg of the title compound. MP: 202°–203° C.

EXAMPLE 3

(S)—N—[[3-[4-[4-(2-Benzoxazolyl)-1-piperazinyl]-3-fluorophenyl]-2-oxo-5-oxazolidinyl]methyl] acetamide

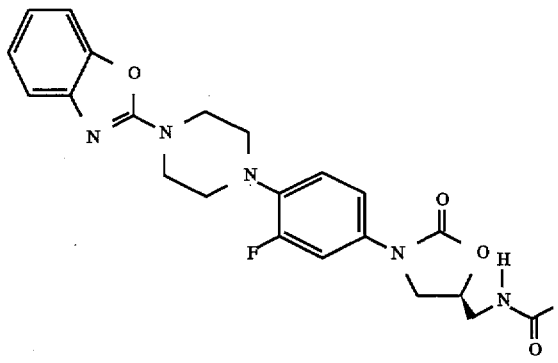

The starting material XLII (where $X^1$ is fluorine (F), $X^2$ is hydrogen (H), and $R^1$ is acetyl ($COCH_3$)) (450 mg, 1.34 mmol) is dissolved into 8 mL of DMSO. The solution is treated with $K_2HPO_4$ (350 mg, 2.01 mmol) followed by 2-chlorobenzoxazole (216 mg, 1.40 mmol). The mixture is heated to 90° C. for 1 hour. After this time TLC shows starting material is consumed. The reaction mixture is poured into a separatory funnel along with $CH_2Cl_2$. The mixture is washed with $H_2O$ and brine. The organic phase is separated and dried over anhydrous $Na_2SO_4$. Filtration and concentration of the organic phase gives a solid that is purified by radial chromatography on silica gel, eluting with 5% MeOH/CHCl$_3$, to give 412 mg of the title compound. MP: 223°–224° C.

EXAMPLE 4

(S)—N—[[3-[3-Fluoro-4-[4-(5-nitrobenzoxazol-2-yl)-1-piperazinyl]phenyl]-2-oxo-5-oxazolidinyl] methyl]acetamide

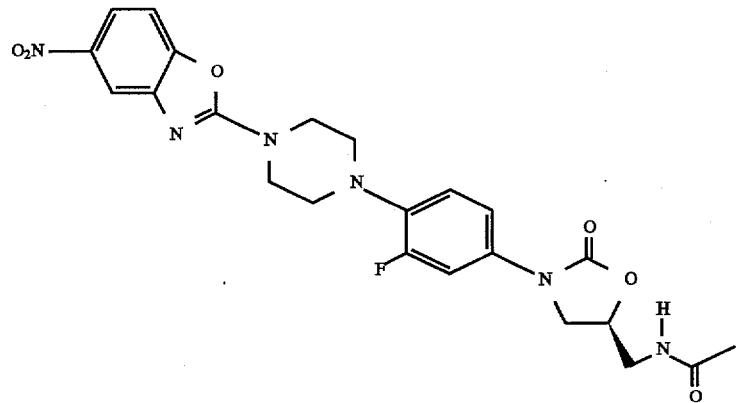

The starting material XLII (where $X^1$ is fluorine (F), $X^2$ is hydrogen (H), and $R^1$ is acetyl ($COCH_3$)) (336 mg, 1.0 mmol) is dissolved into 8 mL of DMSO. The reaction mixture is treated with powdered $K_2CO_3$ (276 mg, 2.0 mmol) and 2-chloro-5-nitrobenzoxazole (276 mg, 2.0 mmol). The mixture is heated to 90° C. for 1 hour. After this time TLC shows starting material is consumed. The reaction mixture is poured into a separatory funnel along with $CH_2Cl_2$. The mixture is washed with $H_2O$ and brine. The organic phase is separated and dried over anhydrous $Na_2SO_4$. Filtration and concentration gives a solid that is purified by radial chromatography on silica gel eluting with 3% MeOH/CHCl$_3$. This results in a yellow solid that is recrystallized from EtOAc to give 251 mg of the title compound. MP: 224°–225° C.

EXAMPLE 5

(S)—N—[[3-[3-Fluoro-4-[4-(2-thiazolyl)-1-piperazinyl]phenyl]-2-oxo-5-oxazolidinyl]methyl] acetamide

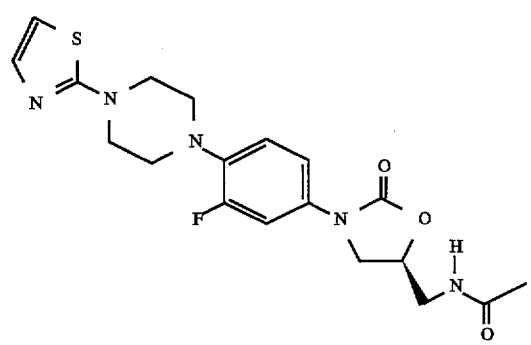

The starting material XLII (where $X^1$ is fluorine (F), $X^2$ is hydrogen (H), and $R^1$ is acetyl ($COCH_3$)) (300 mg, 0.80 mmol) is slurried into 4 mL of dry DMF in a resealable tube. The slurry is treated with $Et_3N$ (244 mg, 2.41 mmol) and 2-bromothiazole (262 mg, 1.6 mmol). The tube is sealed and the mixture is heated to 100° C. The mixture becomes homogeneous upon heating. The reaction is maintained at this temperature for 15 hours. After this time TLC shows starting material is consumed. The DMF is removed under reduced pressure and the residue is dissolved into $CH_2Cl_2$. The mixture is washed with $H_2O$ and brine. The organic phase is separated and dried over anhydrous $Na_2SO_4$. Filtration and concentration gives a solid that is purified by radial chromatography on silica gel, eluting with 3% MeOH/CHCl$_3$, to provide 121 mg of the title compound. MP: 205°–206° C.

EXAMPLE 6

(S)—N—[[3-[3-Fluoro-4-[4-(6-nitrobenzothiazol-2-yl)-1-piperazinyl]phenyl]-2-oxo-5-oxazolidinyl]methyl]acetamide

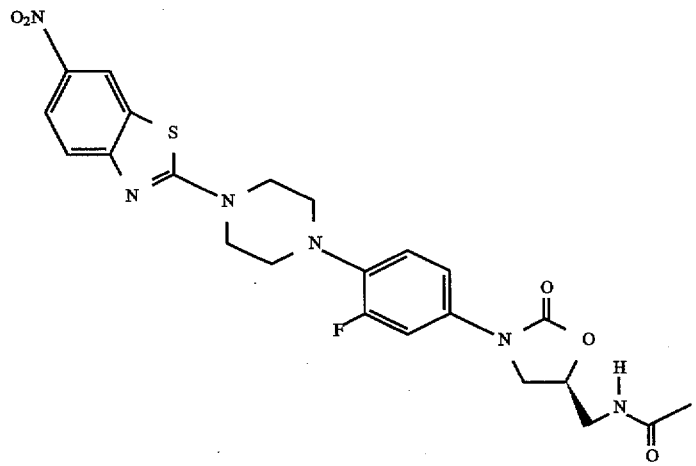

The starting material XLII (where $X^1$ is fluorine (F), $X^2$ is hydrogen (H), and $R^1$ is acetyl ($COCH_3$)) (350 mg, 0.94 mmol) is dissolved into 8 mL of DMSO. The solution is treated with powdered $K_2CO_3$ (259 mg, 1.9 mmol) followed by 2-chloro-6-nitrobenzothiazole (215 mg, 1.0 mmol). The mixture is stirred at room temperature for 16 hours. After this time TLC shows starting material is consumed. The reaction mixture is poured into a separatory funnel along with $CH_2Cl_2$. The mixture is washed with $H_2O$ and brine. The organic phase is separated and dried over anhydrous $Na_2SO_4$. Filtration and concentration gives a solid that is purified by radial chromatography on silica gel, eluting with 3% $MeOH/CHCl_3$, to give 371 mg of the title compound. MP: 216°–217° C.

EXAMPLE 7

(S)—N—[[3-[3-Fluoro-4-[4-(5-fluorobenzoxazol-2-yl)-1-piperazinyl]phenyl]-2-oxo-5-oxazolidinyl]methyl]acetamide

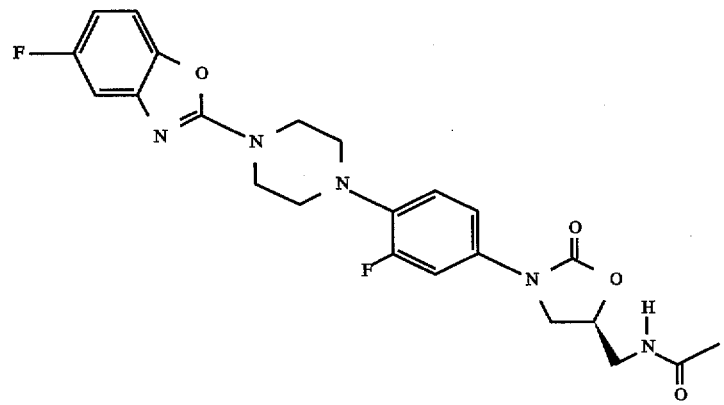

Step 1

4-Fluoro-6-nitrophenol (5.0 g, 31.8 mmol) is dissolved into 25 mL of MeOH. The solution is degassed by evacuation and flushing with $N_2$ (3 times). The solution is treated with 10% Pd/C (750 mg, 15 wt. %) followed by degassing and flushing with $H_2$. The reaction is maintained at atmospheric $H_2$ pressure for 16 hours. After this time TLC shows some starting material remains. An additional 300 mg of 10% Pd/C is added and stirring is continued under atmospheric $H_2$ pressure until starting material is consumed (3.5 hours longer). The reaction is filtered through celite and the solution of crude aniline is used without delay. The solution of crude aniline is added to a solution of potassium methyl xanthate (35 mmol) in 4:1 methanol/$H_2O$. The mixture is heated to reflux for 18 hours. After this time the mixture is treated with 4.5 mL of glacial acetic acid and the mixture is allowed to cool. The MeOH is removed under reduced pressure, and the solid is purified by chromatography on silica gel eluting with 5:1 hexane/EtOAc. This leads to isolation of 3.4 g of 2-mercapto-5-fluorobenzoxazole. MP: 237°–238° C.

Step 2

The 2-mercapto-5-fluorobenzoxazole (2.0 g, 11.8 mmol) is slurried into $POCl_3$ (9.7 mL, 104 mmol). The slurry is treated with $PCl_5$ (3.0 g, 14.2 mmol) and 5.0 mL of anhydrous CH₂Cl₂. The mixture is stirred at room temperature for 5.5 hours. After this time excess POCl₃ is removed under reduced pressure. The residue is treated with saturated aqueous NaHCO₃ and the mixture is poured into a separatory funnel. The mixture is extracted with EtOAc and the combined extracts are washed with brine and dried over anhydrous Na₂SO₄. Filtration and concentration gives 1.76 g of 2-chloro-5-fluorobenzoxazole as a waxy solid. The crude chloride is used in the piperazine displacement reaction.

Step 3

The starting material XLII (where $X^1$ is fluorine (F), $X^2$ is hydrogen (H), and $R^1$ is acetyl (COCH₃)) (400 mg, 1.1 mmol) is dissolved into 10 mL of dry DMSO. The slurry is treated with the crude chloride described above (276 mg, 1.60 mmol) and powdered K₂CO₃ (304 mg, 2.2 mmol). The mixture is heated to 90° C. for 1 hour. After this time TLC shows starting material is consumed. The reaction mixture is poured into a separatory funnel along with CH₂Cl₂. The mixture is washed with H₂O and brine. The organic phase is separated and dried over anhydrous Na₂SO₄. The solution is filtered and concentrated to give a solid that is triturated with CH₂Cl₂/EtOAc. The solids are filtered and washed with 3:1 Et₂O/EtOAc and dried in vacuo to give 378 mg of the title compound. MP: 226°–228° C.

EXAMPLE 8

(S)—N—[[3-[3-Fluoro-4-[4-(6-fluorobenzoxazol-2-yl)-1-piperazinyl]phenyl]-2-oxo-5-oxazolidinyl]methyl]acetamide

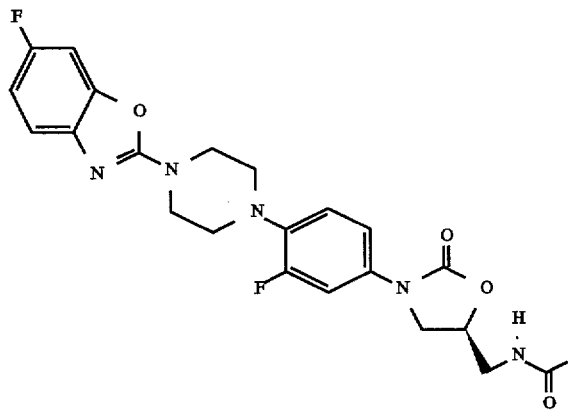

Step 1

The 2-mercapto-6-fluorobenzoxazole is prepared from 3-fluoro-6-nitrophenol as described in the previous example. MP: 248°–250° C.

Step 2

This material is converted to 2-chloro-6-fluorobenzoxazole as described in the previous example. This material is used without purification.

Step 3

The starting material XLII (where $X^1$ is fluorine (F), $X^2$ is hydrogen (H), and $R^1$ is acetyl (COCH₃)) (400 mg, 1.07 mmol) is dissolved into 10 mL of dry DMSO. The solution is treated with powdered K₂CO₃ (296 mg, 2.14 mmol) and 2-chloro-6-fluorobenzoxazole (276 mg, 1.61 mmol). The mixture is heated to 90° C. for 2 hours. After this time TLC shows starting material is consumed. The reaction mixture is poured into a separatory funnel along with CH₂Cl₂. The mixture is washed with H₂O and brine. The organic phase is separated and dried over anhydrous Na₂SO₄. The solution is filtered and concentrated to give a solid that is purified by radial chromatography eluting with a gradient of 1–4% MeOH/CHCl₃. This gives 406 mg of the title compound as a solid. MP: 233°–234° C.

EXAMPLE 9

(S)—N—[[3-[3-Fluoro-4-[4-(7-fluorobenzoxazol-2-yl)-1-piperazinyl]phenyl]-2-oxo-5-oxazolidinyl]methyl]acetamide

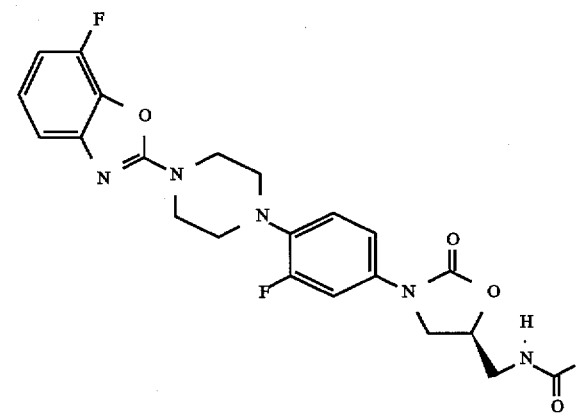

Step 1

The 2-mercapto-7-fluorobenzoxazole is prepared from 2-fluoro-6-nitrophenol as described earlier. MP: 232°–234° C.

Step 2

This material is converted to 2-chloro-7-fluorobenzoxazole as described earlier. This material is used without purification.

Step 3

The starting material XLII (where $X^1$ is fluorine (F), $X^2$ is hydrogen (H), and $R^1$ is acetyl (COCH₃)) (450 mg, 1.21 mmol) is dissolved into dry DMSO. The solution is treated with powdered K₂CO₃ (334 mg, 2.41 mmol) and 2-chloro-7-fluorobenzoxazole (311 mg, 1.82 mmol). The mixture is heated to 90° C. for 2 hours. After this time TLC shows starting material is consumed. The reaction mixture is poured into a separatory funnel along with CH₂Cl₂. The mixture is washed with H₂O and brine. The organic phase is separated and dried over anhydrous Na₂SO₄. The solution is filtered and concentrated to give a wet slurry. Added 3 mL of CH₂Cl₂ and the product is precipitated by the addition of Et₂O. The solids were filtered and washed with Et₂O and dried in vacuo to give 531 mg of the title compound. MP: 201°–202° C.

EXAMPLE 10

(S)—N—[[3-[3-Fluoro-4-[4-(6,7-difluorobenzoxazol-2-yl)-1-piperazinyl]phenyl]-2-oxo-5-oxazolidinyl]methyl]acetamide

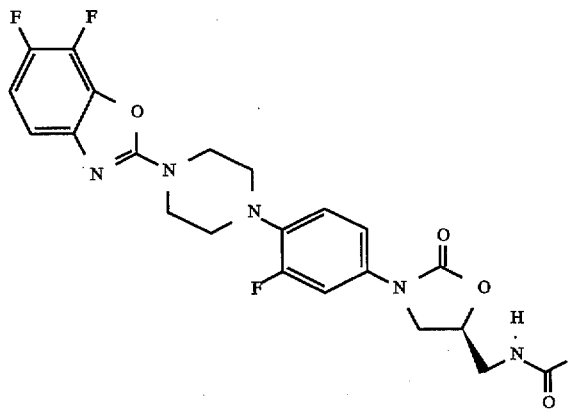

Step 1

The 2-mercapto-6,7-difluorobenzoxazole is prepared from 2,3-difluoro-6-nitrophenol as described earlier. MP: 209°–210° C.

Step 2

This material is converted to 2-chloro-6,7-difluorobenzoxazole as described earlier. This material is used without purification.

Step 3

The starting material XLII (where $X^1$ is fluorine (F), $X^2$ is hydrogen (H), and $R^1$ is acetyl ($COCH_3$)) (750 mg, 2.01 mmol) is dissolved into 10 mL of dry DMSO. The solution is treated with powdered $K_2CO_3$ (556 mg, 4.02 mmol) and 2-chloro-6,7-difluorobenzoxazole (573 mg, 3.02 mmol). The mixture is heated to 90° C. for 1 hour. After this time TLC shows starting material is consumed. The reaction mixture is poured into a separatory funnel along with $CH_2Cl_2$. The mixture is washed with $H_2O$ and brine. The organic phase is separated and dried over anhydrous $Na_2SO_4$. The solution is filtered and concentrated to a brown sludge that is purified by radial chromatography on silica gel, eluting with 10% $CH_3CN$/2% $MeOH/CHCl_3$, to provide 483 mg of the title compound. MP: 213°–214° C.

EXAMPLE 11

(S)—N—[[3-[4-[4-(4,5-Dihydro-2-thiazolyl)-1-piperazinyl]-3-fluorophenyl]-2-oxo-5-oxazolidinyl]methyl]acetamide

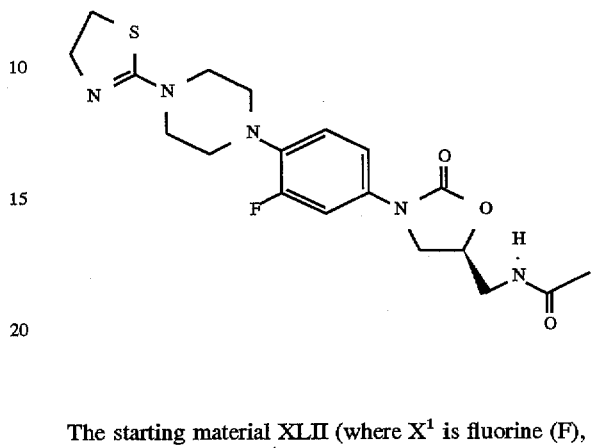

The starting material XLII (where $X^1$ is fluorine (F), $X^2$ is hydrogen (H), and $R^1$ is acetyl ($COCH_3$)) (0.336 g, 1.00 mmol) is dissolved in 7 mL of $CH_2Cl_2$. To this solution is added 2-chloroethylisothiocyanate (0.122 g, 1.00 mmol). After stirring for 18 hours, the reaction is concentrated. The residue is purified by flash chromatography, using 10% $MeOH/CHCl_3$ as eluent to afford 0.196 g of product. MP: 219°–223° C.

EXAMPLE 12

(S)—N—[[3-[4-[4-(4,5-Dihydro-2-oxazolyl)-1-piperazinyl]-3-fluorophenyl]-2-oxo-5-oxazolidinyl]methyl]acetamide

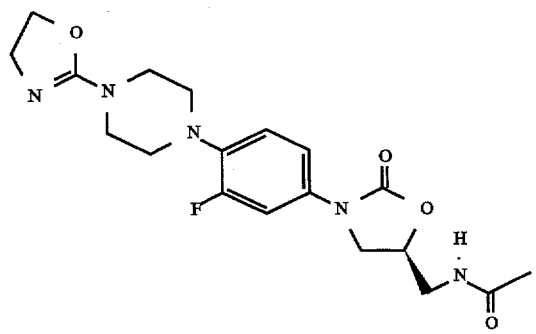

The starting material XLII (where $X^1$ is fluorine (F), $X^2$ is hydrogen (H), and $R^1$ is acetyl ($COCH_3$)) (0.336 g, 1.00 mmol) is dissolved in 5 mL of $CH_2Cl_2$. To this solution is added 2-chloroethylisocyanate (0.106 g, 1.00 mmol). After stirring for 30 min at room temperature, the reaction is concentrated. The residue is dissolved in 15 mL of $CH_3CN$ and $KF$—$Al_2O_3$ is added (0.680 g). This suspension is heated at reflux for 3 h and then filtered and concentrated. The residue is purified by flash chromatography using 10% $CH_3OH/CHCl_3$ as eluent to afford 0.157 g of the product. MP: 230°–234° C. (dec).

EXAMPLE 13

(S)—N—[[3-[4-[3-Fluoro-4-[(1-phenyl-5-tetrazolyl)-1-piperazinyl]phenyl]-2-oxo-5-oxazolidinyl]methyl]acetamide

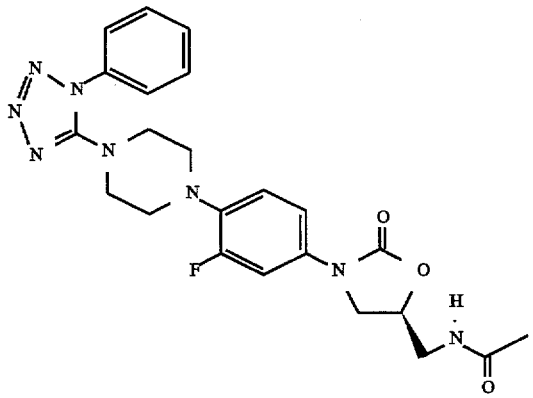

A solution of 5-chloro-1-phenyltetrazole (0.199 g) in 10 mL of $CH_3CN$ is treated with XLII (where $X^1$ is fluorine (F), $X^2$ is hydrogen (H), and $R^1$ is acetyl ($COCH_3$)) (0.372 g) and $Et_3N$ (0.30 mL). The resulting suspension is heated at reflux for 8 h and then additional 5-chloro-1-phenyltetrazole (0.199 g) and $Et_3N$ (0.15 mL) are added. The reaction is heated at reflux for an additional 18 h and then cooled, diluted with ethyl acetate, filtered, and concentrated. The residue is chromatographed on silica gel with 95:5 $CHCl_3$:$CH_3OH$ to afford 0.41 g of the product. MP: 178°–180° C.

EXAMPLE 14

(S)—N—[[3-[4-[3-Fluoro-4-[(methyl-5-tetrazolyl)-1-piperazinyl]phenyl]-2-oxo-5-oxazolidinyl]methyl]acetamide

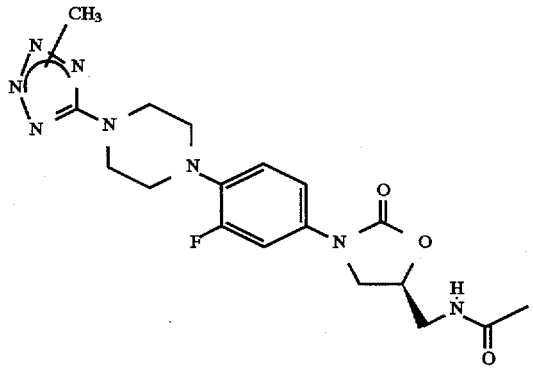

Step 1

To a solution of XLII (where $X^1$ is fluorine (F), $X^2$ is hydrogen (H), and $R^1$ is acetyl ($COCH_3$)) (0.5 g) and sodium acetate (0.55 g) in 40 mL of MeOH at 0° C. is added dropwise a solution of cyanogen bromide (0.16 g) in 10 mL of MeOH. The solution is stirred at 0° C. for 2.5 h and then warmed to room temperature and stirred overnight. The solvents were removed and the resulting solid is partitioned between EtOAc/n-BuOH (1:1) and saturated aqueous $NaHCO_3$. The aqueous layer is extracted with EtOAc, and the combined organic layers are washed with brine, dried ($Na_2SO_4$) and concentrated. The crude product is chromatographed on silica gel with 10% $MeOH/CH_2Cl_2$ to yield 0.371 g of the cyanamide XLV as a white solid. MP: 191°–193° C.

Step 2

A solution of the cyanamide XLV (where $X^1$ is fluorine (F), $X^2$ is hydrogen (H), and $R^1$ is acetyl ($COCH_3$)) (0.12 g) and $NaN_3$ (0.214 g) in 7 ml of EtOH and 1 mL of water are heated at reflux for 72 h and then concentrated. The residue is dissolved in water and the resulting aqueous solution is acidified with acetic acid. The resulting precipitate is filtered and then dissolved in $CHCl_3$/n-BuOH (9:1). The resulting solution is dried and concentrated and the residue is crystallized from MeOH to afford 0.058 g of the tetrazole. MP: 212°–214° C.

Step 3

A suspension of the tetrazole (1.0 g) in 100 mL of methanol is cooled to –5° C. and then treated with excess ethereal diazomethane. The resulting solution is stirred for 2 h during which time it is allowed to warm to room temperature. Excess diazomethane is destroyed by addition of 20% acetic acid in EtOAc. The reaction is diluted with EtOAc and then washed with 5% NaCl solution and 5% $NaHCO_3$ solution. The reaction solution is dried and concentrated, and the residue is crystallized from acetonitrile to give 0.337 g of the methylated tetrazole product in which the position of the methyl group is uncertain. MP: 198°–200° C.

EXAMPLE 15

(S)—N—[[3-[3-Fluoro-4-[4-(4-oxo-2-thiazolinyl-1-piperazinyl]phenyl]-2-oxo-5-oxazolidinyl]methyl] acetamide

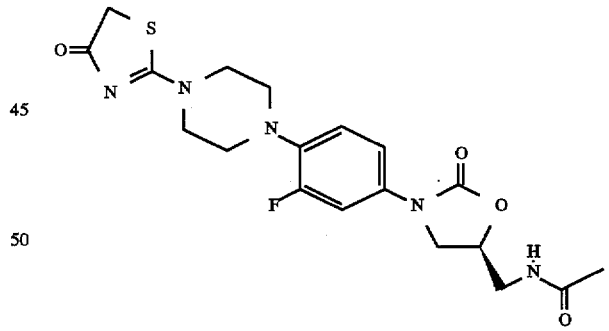

A mixture of XLII (where $X^1$ is fluorine (F), $X^2$ is hydrogen (H), and $R^1$ is acetyl ($COCH_3$)) (0.672 g), acetic acid (0.120 mg), and thiocyanatoacetic acid methyl ester (0.265 g) in 10 mL of absolute EtOH is heated to reflux for 2 hours. The mixture on cooling to room temperature gives a white solid which is filtered and washed with ethanol and anhydrous ether to afford 0.36 g of the thiazolinone. Recrystallization from $MeOH/CHCl_3$ gives 0.330 g of (S)—N—[ [3-[3-fluoro-4-[4-(4-oxo-2-thiazolinyl)-1-piperazinyl] phenyl]-2-oxo-5-oxazolidinyl]methyl]acetamide as a white solid. MP: 225°–227° C.

EXAMPLE 16

(S)—N—[[3-[3-Fluoro-4-[4-(1,3,4-thiadiazol-2-yl)-1-piperazinyl]phenyl]-2-oxo-5-oxazolidinyl]mehtyl]acetamide

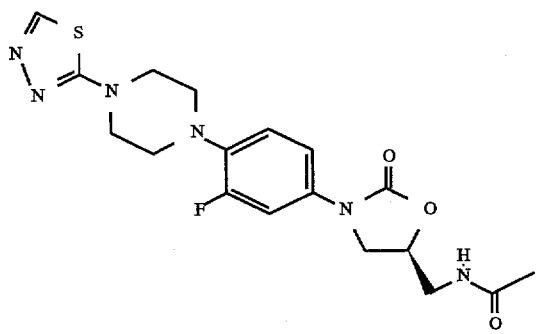

Step 1

2-Bromo-1,3,4-thiadiazole is prepared according to the procedure of Goerdeler (*Chem. Ber.* 1956, 89, 1534–43).

Step 2

A mixture of XLII (where $X^1$ is fluorine (F), $X^2$ is hydrogen (H), and $R^1$ is acetyl (COCH$_3$)) (0.672 g), 2-bromo-1,3,4-thiadiazole (0.370 g), and K$_2$HPO$_4$ (0.720 g) in 20 mL of DMSO is heated to 110° C. for 2 hours and then at room temperature overnight. The above mixture is diluted with 50 mL of CH$_2$Cl$_2$ and washed with water, brine, and then dried over Na$_2$SO$_4$. The mixture is filtered and concentrated to afford a yellow solid. Recrystallization from MeOH/EtOAc gives 0.300 g of (S)—N—[[3-[3-fluoro-4-[4-(1,3,4-thiadiazol-2-yl)-1-piperazinyl]phenyl]-2-oxo-5-oxazolidinyl]methyl]acetamide as a white solid. MP: 206°–208° C.

EXAMPLE 17

(S)—N—[[3-[3-Fluoro-4-[4-(5-methyl-1,3,4-thiadiazol-2-yl)-1-piperazinyl]phenyl]-2-oxo-5-oxazolidinyl]methyl]acetamide

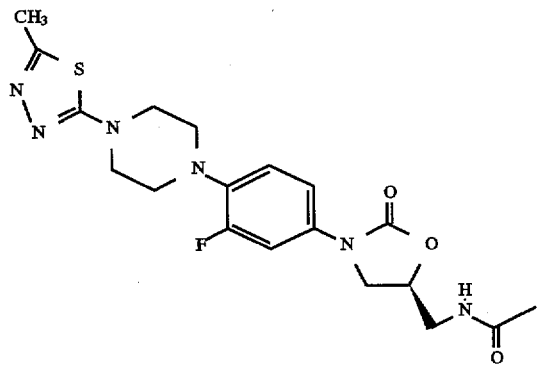

Step 1

2-Bromo-5-methyl-1,3,4-thiadiazole is prepared according to the procedure of Goerdeler (*Chem. Ber.* 1956, 89, 1534–43).

Step 2

A mixture of XLII (where $X^1$ is fluorine (F), $X^2$ is hydrogen (H), and $R^1$ is acetyl (COCH$_3$)) (0.672 g), 2-bromo-5-methyl-1,3,4-thiadiazole (0.396 g), and K$_2$HPO$_4$ (0.720 g) in 20 mL of DMSO is heated to 110° C. for 2 h. The above mixture is poured into water and extracted with three 30 mL portions of CHCl$_3$. The CHCl$_3$ solution is dried over Na$_2$SO$_4$, filtered and concentrated to afford a yellow solid. Purification by column chromatography using 5% CH$_3$OH/CHCl$_3$ as eluent gives 0.410 g of (S)—N—[[3-[3-fluoro-4-[4-(5-methyl-1,3,4-thiadiazol-2-yl)-1-piperazinyl]phenyl]-2-oxo-5-oxazolidinyl]methyl]acetamide as a white solid. MP: 247°–249° C.

EXAMPLE 18

(S)—N—[[3-[4-[4-(5-Amino-1,3,4-thiadiazol-2-yl)-3-fluoro-1-piperazinyl]phenyl]-2-oxo-5-oxazolidinyl]methyl]acetamide

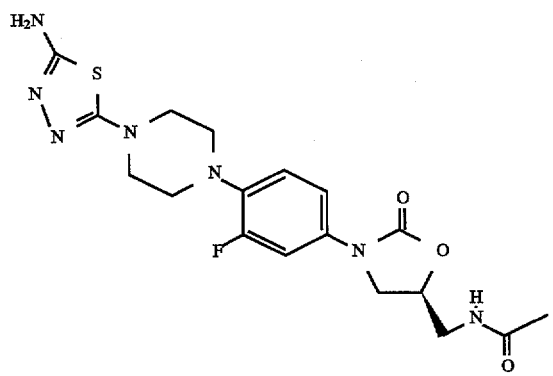

Step 1

2-Amino-5-bromo-1,3,4-thiadiazole is prepared by the method of Werber (*J. Heterocycl. Chem.* 1977, 14, 823–7).

Step 2

A mixture of XLII (where $X^1$ is fluorine (F), $X^2$ is hydrogen (H), and $R^1$ is acetyl (COCH$_3$)) (0.672 g), 2-amino-5-bromo-1,3,4-thiadiazole (0.375 g), and K$_2$HPO$_4$ (0.720 g) in 20 mL of DMSO is heated to 100° C. for 2 hours. The above mixture is poured into 50 mL water and washed with two 50 mL portions of CH$_2$Cl$_2$. The aqueous layer is filtered and the product is washed with anhydrous ether and dried. Recrystallization from MeOH/CHCl$_3$ affords 0.367 g of (S)—N—[[3-[4-[4-(5-amino-1,3,4-thiadiazol-2-yl)-3-fluoro-1-piperazinyl]phenyl]-2-oxo-5-oxazolidinyl]methyl]acetamide as a yellow solid. MP: 228°–230° C.

EXAMPLE 19

(S)—N—[[3-[4-[4-(5-Ethoxycarbonyl-1,3,4-thiadiazol-2-yl)-3-fluoro-1-piperazinyl]phenyl]-2-oxo-5-oxazolidinyl]methyl]acetamide

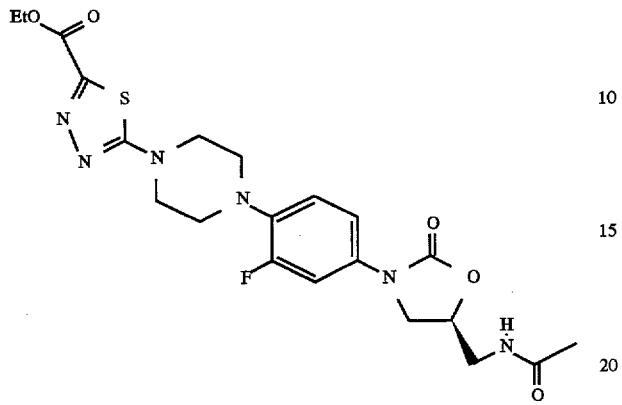

Step 1

Ethyl 2-chloro-1,3,4-thiadiazole-5-carboxylate is prepared according to the procedure of Demaree (*Can. J. Chem.* 1977, 55, 243–250).

Step 2

A mixture of XLII (where $X^1$ is fluorine (F), $X^2$ is hydrogen (H), and $R^1$ is acetyl ($COCH_3$)) (2.0 g), ethyl 2-chloro-1,3,4-thiadiazole-5-carboxylate (1.27 g), and $K_2HPO_4$ (2.16 g) in 50 mL of DMSO is heated to 100° C. for 3 hours. The above mixture is poured ice and then filtered. The product is washed with water, methanol, and anhydrous ether and then dried to afford 2.15 g of (S)—N—[[3-[4-[4-(5-ethoxycarbonyl-1,3,4-thiadiazol-2-yl)-3-fluoro-1-piperazinyl]phenyl]-2-oxo-5-oxazolidinyl]methyl]acetamide. MP: 228°–230° C.

EXAMPLE 20

(S)—N—[[3-[3-Fluoro-4-[4-(5-trifluoromethyl-1,3,4-thiadiazol-2-yl)-1-piperazinyl]phenyl]-2-oxo-5-oxazolidinyl]methyl]acetamide

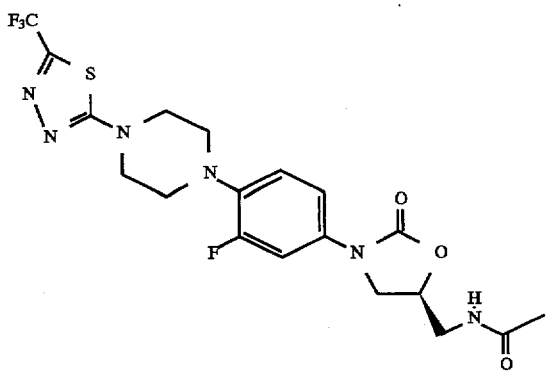

Step 1

2-Bromo-5-trifluoromethyl-1,3,4-thiadiazole is prepared according to the procedure of Dunn (U.S. Pat. No. 3,968, 226).

Step 2

A mixture of XLII (where $X^1$ is fluorine (F), $X^2$ is hydrogen (H), and $R^1$ is acetyl ($COCH_3$)) (1.0 g), 2-bromo-5-trifluoromethyl-1,3,4-thiadiazole (0.56 g), and $K_2HPO_4$ (1.08 g) in 25 mL of DMSO is heated to 100° C. for 3 hours. The above mixture is poured onto ice and then filtered. The product is washed with water, methanol, and anhydrous ether and then dried to afford 1.25 g of the product. MP: 255°–257° C.

EXAMPLE 21

(S)—N—[[3-[4-[4-(5-Aminocarbonyl-1,3,4-thiadiazol-2-yl)-3-fluoro-1-piperazinyl]phenyl]-2-oxo-5-oxazolidinyl]methyl]acetamide

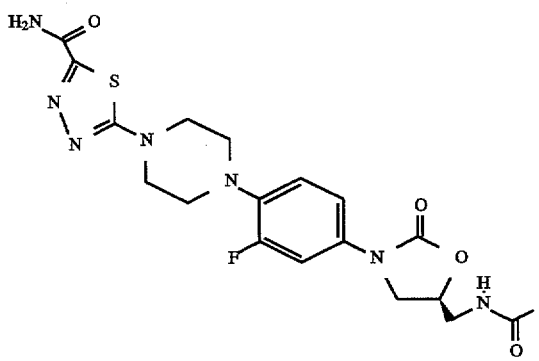

Step 1

2-Chloro-1,3,4-thiadiazole-5-carboxamide is prepared according to the procedure of Demaree (*Can. J. Chem.* 1977, 55, 243–250).

Step 2

A mixture of XLII (where $X^1$ is fluorine (F), $X^2$ is hydrogen (H), and $R^1$ is acetyl ($COCH_3$)) (0.307 g), 2-chloro-1,3,4-thiadiazole-5-carboxamide (0.224 g), and $K_2CO_3$ (0.376 g) in 5 mL of $CH_3CN$ is heated at reflux for 18 hours. The above mixture is diluted with $CH_3OH/CHCl_3$ and filtered. The filtrate is concentrated and the residue is purified by column chromatography (using 5% $CH_3OH/CHCl_3$ as eluent) to afford 0.282 g of (S)—N—[[3-[4-[4-(5-aminocarbonyl-1,3,4-thiadiazol-2-yl)-3-fluoro-1-piperazinyl]phenyl]-2-oxo-5-oxazolidinyl]methyl]acetamide. MP: 230°–232° C.

EXAMPLE 22

(S)—N—[[3-[4-[4-(5-Cyano-1,3,4-thiadiazol-2-yl)-3-fluoro-1-piperazinyl]phenyl]-2-oxo-5-oxazolidinyl]mehtyl]acetamide

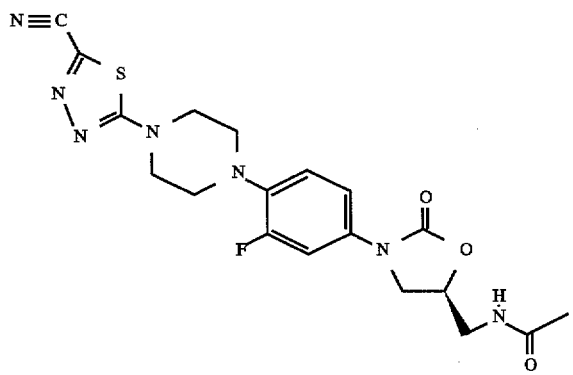

Step 1

A mixture of 2-chloro-1,3,4-thiadiazole-5-carboxamide (1.4 g) in 17 mL of $POCl_3$ is heated at reflux for 18 hours. The reaction mixture is concentrated and the residue is suspended in 25 mL of ethyl acetate. The suspension is cooled in an ice bath and neutralized with saturated, aqueous $NaHCO_3$ (to pH 7). The phases are separated and the aqueous phase is extracted with 20 mL of ethyl acetate. The combined organic phases are dried over $MgSO_4$, filtered and concentrated. The residue is purified by column chromatography (using 30% ethyl acetate/hexane as eluent) to afford 0.832 g of 2-cyano-5-chloro-1,3,4-thiadiazole. MP: 65°–67° C.

Step 2

A mixture of XLII (where $X^1$ is fluorine (F), $X^2$ is hydrogen (H), and $R^1$ is acetyl ($COCH_3$)) (0.344 g), 2-cyano-5-chloro-1,3,4-thiadiazole (0.178 g), and diisopropylethylamine (0.198 g) in 7 mL of $CH_3CN$ is heated at reflux for 18 hours. On cooling, a solid precipitates. This solid is filtered, washed with ether and dried. The solid is recrystallized from methanol/ethyl acetate to afford 0.353 g of (S)—N—[[3-[4-[4-(5-cyano-1,3,4-thiadiazol-2-yl)-3-fluoro-1-piperazinyl]phenyl]-2-oxo-5-oxazolidinyl]methyl]acetamide. MP: 200°–202° C.

EXAMPLE 23

(S)—N—[[3-[3-Fluoro-4-[4-(5-methylthio-1,3,4-thiadiazol-2-yl)-1-piperazinyl]phenyl]-2-oxo-5-oxazolidinyl]methyl]acetamide

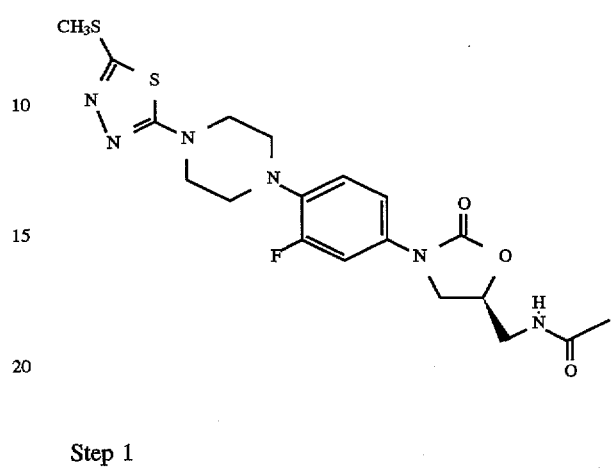

Step 1

5-Amino-1,3,4-thiadiazole-2-thiol (10.1 g) is dissolved in 31 mL of 20% KOH in ethanol and 6.1 mL of water. This solution is cooled in an ice bath and stirred while dimethyl sulfate (7.7 mL) is added dropwise. The reaction is stirred in an ice bath for an additional hour and the filtered. The solid is washed with 50% ethanol/water and dried. Recrystallization from ethanol give 4.8 g of 5-amino-2-methylthio-1,3,4-thiadiazole.

Step 2

A mixture of 5-amino-2-methylthio-1,3,4-thiadiazole (1.36 g) and $NaNO_2$ (2.93 g) is added over 1 hour to a suspension of copper powder (0.088 g) in 48% HBr (14.4 mL) which is cooled to −13° C. This reaction is stirred for 45 minutes at −13° C. and then for 1.5 hours at room temperature. The reaction is cooled in an ice bath and neutralized with 50% NaOH solution (to pH 10). Saturated, aqueous $NaHSO_3$ is added until the reaction no longer gives a positive reaction with starch-iodine test paper. The mixture is then brought to pH 1 with concentrated HCl and extracted with three 75 mL portions of ethyl acetate. The combined organic phases are washed with brine, dried over $MgSO_4$, filtered, and concentrated. The residue is purified by column chromatography (using 5% ethyl acetate/hexane as eluent) to afford 1.09 g of 5-bromo-2-methylthio-1,3,4-thiadiazole Step 3

A mixture of XLII (where $X^1$ is fluorine (F), $X^2$ is hydrogen (H), and $R^1$ is acetyl ($COCH_3$)) (0.433 g), 5-bromo-2-methylthio-1,3,4-thiadiazole (0.326 g), and diisopropylethylamine (0.250 g) in 8.6 mL of $CH_3CN$ is heated at reflux for 42 hours. On cooling, a solid precipitates. This solid is filtered, washed with ether and dried. The solid is purified by column chromatography (using 5% methanol/ethyl acetate as eluent) to afford 0.310 g of (S)—N—[[3-[3-fluoro-4-[4-(5-methylthio-1,3,4-thiadiazol-2-yl)-1-piperazinyl]phenyl]-2-oxo-5-oxazolidinyl]methyl]acetamide. Mp 222°–223° C.

EXAMPLE 24

(S)—N—[[3-[3-Fluoro-4-[4-(5-oxo-1,3,4-thiadiazol-2-yl)-1-piperazinyl]phenyl]-2-oxo-5-oxazolidinyl]methyl]acetamide

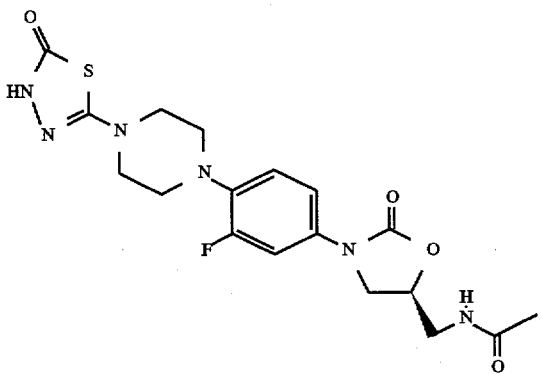

Step 1

S-methylhydrazinecarbodithiate is prepared according to the procedure of Kubaishi (*Can. J. Chem.*, 1994, 72, 1785–8).

Step 2

A mixture of XLII (where $X^1$ is fluorine (F), $X^2$ is hydrogen (H), and $R^1$ is acetyl ($COCH_3$)) (2.00 g) and S-methylhydrazinecarbodithiate (0.799 g) in 40 mL of $CH_3OH$ is heated at reflux for 91 hours. The solid precipitate is filtered, washed with $CH_3OH$ and dried to afford 1.725 g of the thiosemicarbazide of XLII. MP: 191°–192° C.

Step 3

A mixture of the thiosemicarbazide of XLII (0.615 g) and phosgene (0.78 mL of a 20% solution in toluene) in 20 mL of toluene is heated at 80° C. for 1 hour and then stirred at room temperature for 18 hours. The precipitate was isolated by filtration, washed with toluene and ether and dried. The solid is purified by column chromatography (using 15% MeOH/$CHCl_3$ as eluent) to afford 0.206 g of (S)—N—[[3-[3-fluoro-4-[4-(5-oxo-1,3,4-thiadiazol-2-yl)-1-piperazinyl]phenyl]-2-oxo-5-oxazolidinyl]methyl]acetamide. MP: 173°–175° C.

EXAMPLE 25

(S)—N—[[3-[3-Fluoro-4-[4-(3-methyl-1,2,4-thiadiazol-5-yl-1-piperazinyl]phenyl]-2-oxo-5-oxazolidinyl]methyl]acetamide

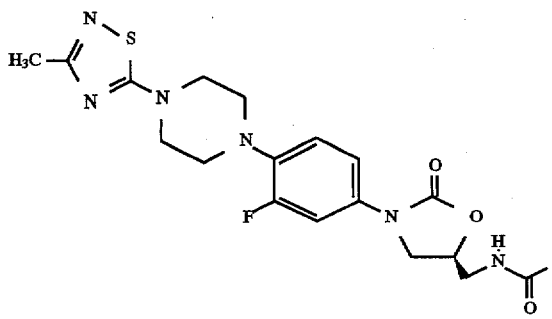

Step 1

5-Chloro-3-methyl-1,2,4-thiadiazole is prepared according to the procedure of Elslager (*J. Her. Chem.* 1973, 10, 611).

Step 2

A mixture of XLII (where $X^1$ is fluorine (F), $X^2$ is hydrogen (H), and $R^1$ is acetyl ($COCH_3$)) (0.505 g), 5-chloro-3-methyl-1,2,4-thiadiazole (0.360 g), and $K_2HPO_4$ (0.525 g) in 15 mL of DMSO is heated to 100° C. for 2 hours. The above mixture is poured into water and extracted with two 50 mL portions of $CHCl_3$. The $CHCl_3$ solution is washed with water and brine and then dried over $Na_2SO_4$, filtered and conc in vacuo to afford a dark oil. Purification by column chromatography using 5% $CH_3OH/CHCl_3$ as eluent gives 0.470 g of (S)—N—[[3-[3-fluoro-4-[4-(3-methyl-1,2,4-thiadiazol-5-yl)-1-piperazinyl]phenyl]-2-oxo-5-oxazolidinyl]methyl]acetamide as a white solid. MP: 168°–170° C.

EXAMPLE 26

(S)—N—[[3-[3-Fluoro-4-[4-(2-phenyl-3-oxo-1,2,4-thiadiazol-5-yl)-1-piperazinyl]phenyl]-2-oxo-5-oxazolidinyl]methyl]acetamide

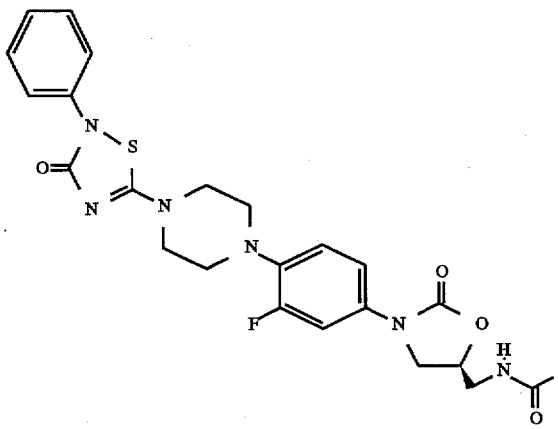

Step 1

5-Chloro-2-phenyl-1,2,4-thiadiazol-3-one is prepared according to the procedure of Keilen (*Acta Chem. Scand. B* 1988, 42, 362–6).

Step 2

A mixture of XLII (where $X^1$ is fluorine (F), $X^2$ is hydrogen (H), and $R^1$ is acetyl ($COCH_3$)) (0.670 g), 5-chloro-2-phenyl-1,2,4-thiadiazol-3-one (0.530 g), and $K_2HPO_4$ (0.815 g) in 20 mL of DMSO is heated to 100° C. for 3 hours. The reaction is poured onto ice and the solid precipitate is isolated by filtration. The solid is washed with water, methanol, and ether. The solid is purified by column chromatography using 5% $CH_3OH$ (saturated with $NH_3$)/$CHCl_3$ as eluent to give 0.400 g of (S)—N—[[3-[3-fluoro-4-[4-(2-phenyl-3oxo-1,2,4-thiadiazol-5-yl)-1-piperazinyl]phenyl]-2-oxo-5-oxazolidinyl]methyl]acetamide as a white solid. MP: 245°–247° C.

EXAMPLE 27

(S)—N—[[3-[3-Fluoro-4-[4-(5-methyl-1,3,4-oxadiazol-2-yl)-1-piperazinyl]phenyl]-2-oxo-5-oxazolidinyl]methyl]acetamide

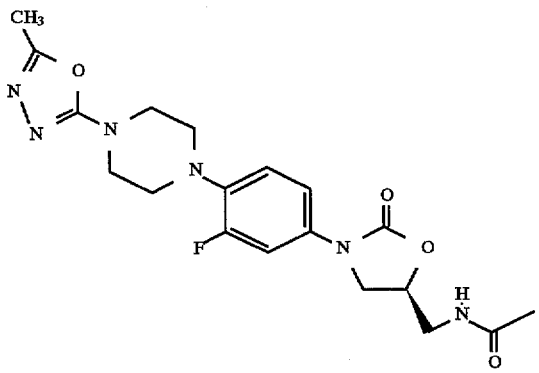

Step 1

5-Methanesulfonyl-2-methyl-1,3,4-oxadiazole is prepared by the method of Confalone (*J. Am. Chem. Soc.* 1983, 105, 902–6). MP: 70°–71° C.

Step 2

A mixture of XLII (where $X^1$ is fluorine (F), $X^2$ is hydrogen (H), and $R^1$ is acetyl (COCH$_3$)) (1.00 g), 5-methanesulfonyl-2-methyl-1,3,4-oxadiazole (0.648 g), and K$_2$HPO$_4$ (1.04 g) in 15 mL of DMSO is heated to 100° C. for 2 hours. The mixture is cooled and diluted with 50 mL of water and then extracted with three 50 mL portions of CH$_2$Cl$_2$. The combined organic phases are dried over MgSO$_4$, filtered and concentrated. Purification by column chromatography using 5% CH$_3$OH/CHCl$_3$ as eluent gives 0.575 g of (S)—N—[[3-[3-fluoro-4-[4-(5-methyl-1,3,4-oxadiazol-2-yl)-1-piperazinyl]phenyl]-2-oxo-5-oxazolidinyl]methyl]acetamide as a white solid. MP: 212°–214° C.

EXAMPLE 28

(S)—N—[[3-[4-[4-(5-Ethyl-1,3,4-thiadiazol-2-yl)-1-piperazinyl]-3-fluoro-phenyl]-2-oxo-5-oxazolidinyl]methyl]acetamide

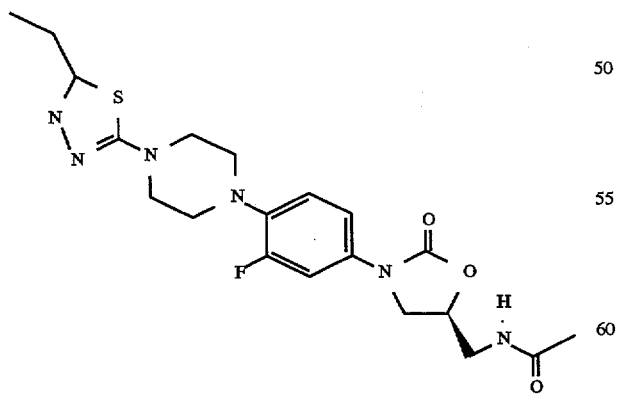

A mixture of the thiosemicarbazide prepared in Step 2 of Example 24 (0.151 g) and propionyl chloride (0.060 g) in 3 mL of THF is heated at reflux for one hour. The precipate is isolated by filtration, washed with THF, and dried. The solid is purified by column chromatography using 2.5% CH$_3$OH/CHCl$_3$ as eluent to afford 0.110 g of (S)—N—[[3-[4-[4-(5-ethyl-1,3,4-thiadiazol-2-yl)-1-piperazinyl]-3-fluorophenyl]-2-oxo-5-oxazolidinyl]methyl]acetamide as a white solid. MP: 237°–238° C.

EXAMPLE 29

(S)—N—[[3-[3-Fluoro-4-[4-(5-propyl-1,3,4-thiadiazol-2-yl)-1-piperazinyl]-phenyl]-2-oxo-5-oxazolidinyl]methyl]acetamide

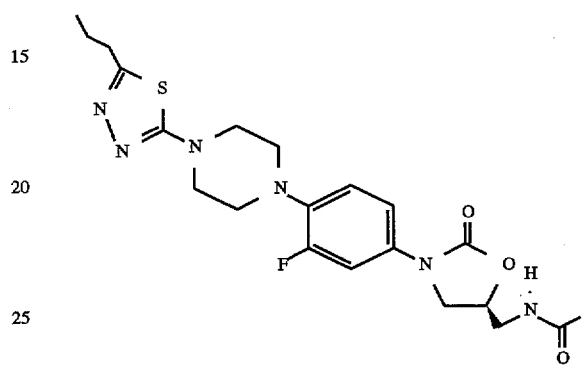

A mixture of the thiosemicarbazide prepared in Step 2 of Example 24 (0.302 g) and butyryl chloride (0.137 g) in 7 mL of THF is heated at reflux for one hour. The precipate is isolated by filtration and washed well with THF. The solid is purified by column chromatography using 2.5% CH$_3$OH/CHCl$_3$ as eluent to afford g of (S)—N—[[3-[3-fluoro-4-[4-(5-propyl-1,3,4-thiadiazol-2-yl)-1-piperazinyl]-phenyl]-2-oxo-5-oxazolidinyl]methyl]acetamide as a white solid. MP: 208°–209° C.

EXAMPLE 30

(S)—N—[[3-[3-Fluoro-4-[4-(5-(1-methyl)ethyl-1,3,4-thiadiazol-2-yl)-1-piperazinyl]-phenyl]-2-oxo-5-oxazolidinyl]methyl]acetamide

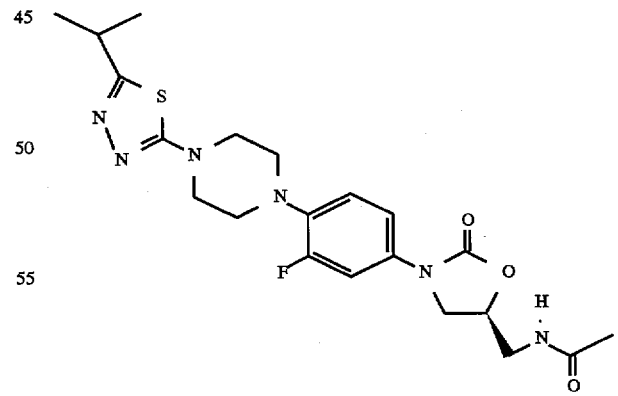

A mixture of the thiosemicarbazide prepared in Step 2 of Example 24 (0.500 g) and 3 mL of isobutyryl chloride is heated at reflux for 30 minutes. The reaction is diluted with 20 mL of CHCl$_3$ and washed with saturated, aqueous Na$_2$CO$_3$. The phases are separated and the aqueous phase is extracted with two 25 mL portions of CHCl$_3$. The combined organic phases are dried over MgSO₄, filtered, and concentrated. The residue is purified by column chromatography using 2% CH₃OH/CHCl₃ as eluent to afford 0.297 g of (S)—N—[[3-[3-fluoro-4-[4-(5-(1-methyl)ethyl-1,3,4-thiadiazol-2-yl)-1-piperazinyl]-phenyl]-2-oxo-5-oxazolidinyl]methyl]acetamide as a white solid. MP: 214°–215° C.

EXAMPLE 31

(S)—N—[[3-[4-[4-(5-Cyclopropyl-1,3,4-thiadiazol-2-yl)-1-piperazinyl]-3-fluoro-phenyl]-2-oxo-5-oxazolidinyl]methyl]acetamide

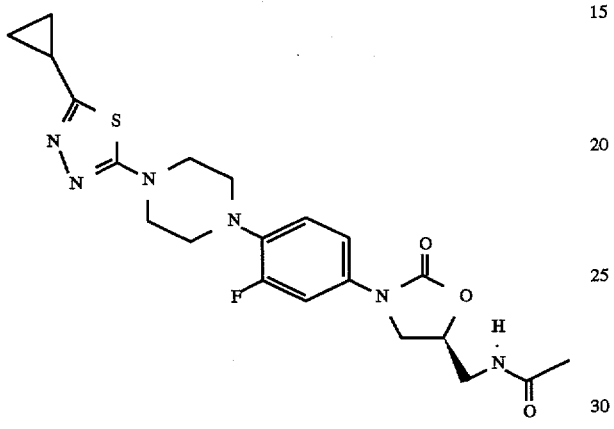

A mixture of the thiosemicarbazide prepared in Step 2 of Example 24 (0.500 g) and 3 mL of propionyl chloride is heated at 90° C. for one hour. The reaction is diluted with 20 mL of ether and the precipate is isolated by filtration. The solid is washed with ether and dried. The solid is purified by column chromatography using 2.5% CH₃OH/CHCl₃ as eluent to afford 0.151 g of (S)—N—[[3-[4-[4-(5-cyclopropyl-1,3,4-thiadiazol-2-yl)-1-piperazinyl]-3-fluoro-phenyl]-2-oxo-5-oxazolidinyl]methyl]acetamide as a white solid. MP: 217°–218° C.

What is claimed is:

1. A compound of structural Formula I:

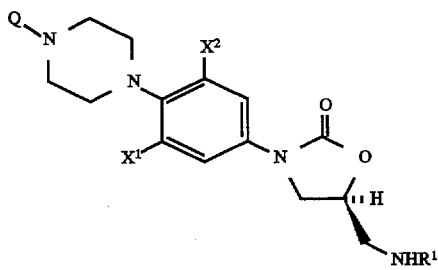

or pharmaceutically acceptable salts thereof wherein:

R¹ is (a) —CHO,
(b) —COCH₃,
(c) —COCHCl₂,
(d) —COCHF₂,
(e) —CO₂CH₃,
(f) —SO₂CH₃, or
(g) —COCH₂OH;

X¹ and X² are independently H, F, or Cl;

Q is selected from (a) oxazole: 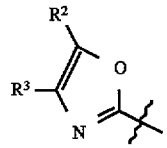 II (b) oxazol-4-one: 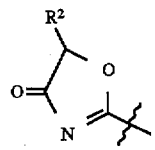 III (c) 4,5-dihydrooxazole: 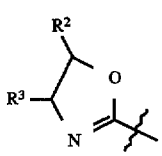 IV (d) benzoxazole: 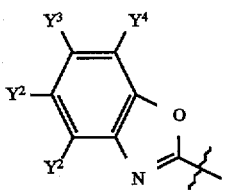 V (e) 1,3,4-oxadiazole: 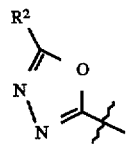 VI (f) 1,2,4-oxadiazole (attached to piperazine at C5): 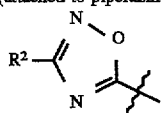 VII (g) 1,2,4-oxadiazole (attached to piperazine at C3): 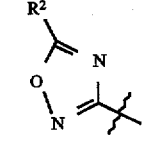 VIII (h) 1,2,4-oxadiazol-5-one: 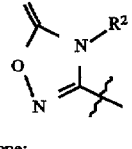 IX (i) 1,3,4-oxathiazol-2-one: 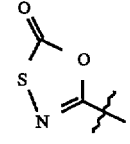 X -continued (j) thiazole:
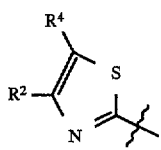
XI (k) benzothiazole:
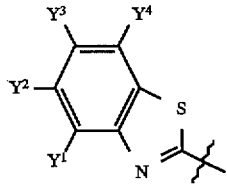
XII (l) thiazol-4-one:
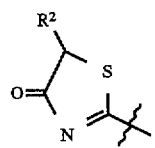
XIII (m) thiazoledione:
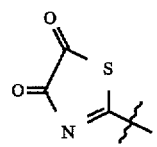
XIV (n) thiazoline:
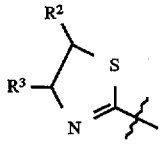
XV (o) 1,3,4-thiadiazole:
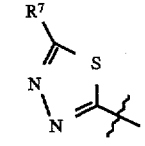
XVI (p) 1,3,4-thiadiazol-2-one:
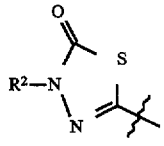
XVII (q) 1,2,4-thiadiazole:
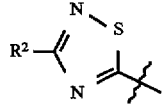
XVIII (r) 1,2,4-thiadiazol-3-one:
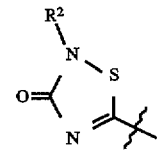
XIX (s) 1,2,5-thiadiazole:
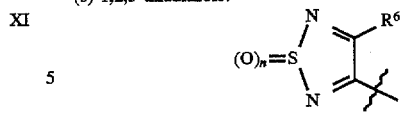
XX (t) 1,2,3,4-thiatriazole:
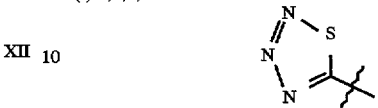
XXI (u) 1,2,4-dithiazolone:
XXII (v) imidazole:
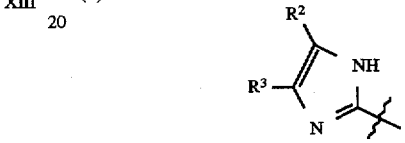
XXIII (w) benzimidazole:
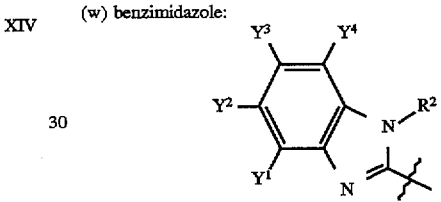
XXIV (x) imidazol-4-one:
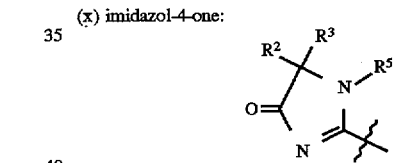
XXV (y) 1,2,4-triazole (Type 1):
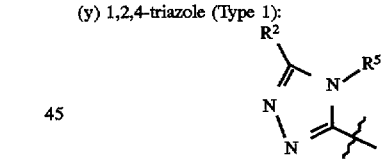
XXVI (z) 1,2,4-triazole (Type 2):
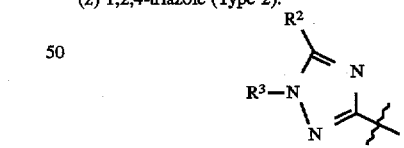
XXVII (aa) 1,2,4-triazole (Type 3):
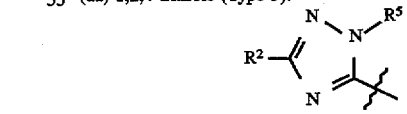
XXVIII (bb) 1,2,4-triazolone:
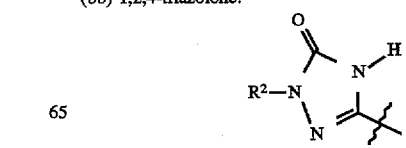
XXIX (cc) 1,2,3-triazole:
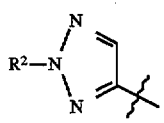

(dd) tetrazole (Type 1):
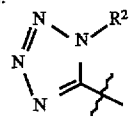

(ee) tetrazole (Type 2):
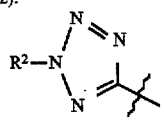

(ff) isoindol-7-ones:
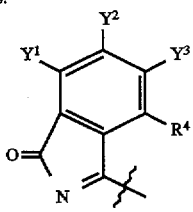

(gg) pyrazol-3-one:
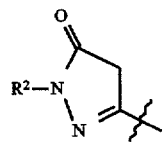

(hh) pyrazoline:
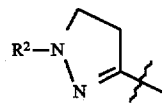

(ii) pyrazole:
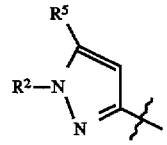

(jj) indazole:
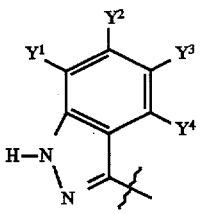

(kk) benzoisothiazole:
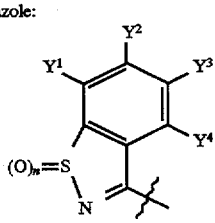

(ll) isoxazole:
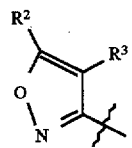

(mm) benzisoxazole:
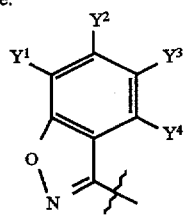

or (nn) 1,2,3-oxathiazole-1-oxide:
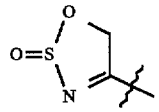

wherein $R^2$ and $R^3$ are independently
(a) H— (except where Q is formula XXXI or XXXII),
(b) $(C_1-C_8)$alkyl-,
(c) $(C_3-C_5$ cycloalkyl)—, or
(d) phenyl;
or $R^2$ and $R^3$ taken together are —$CH_2$—$(CH_2)_m$—;
wherein $R^4$ is
(a) H—,
(b) $(C_1-C_8$ alkyl)—,
(c) $(C_3-C_5$ cycloalkyl)—,
(d) phenyl-,
(e) $O_2N$—, or
(f) $CH_3CH_2OC(O)$—;
or $R^2$ and $R^4$ taken together are —$CH_2$—$(CH_2)_m$—;
wherein $R^5$ is
(a) H—,
(b) $(C_1-C_8$ alkyl)—,
(c) $(C_3-C_5$ cycloalkyl)—, or
(d) phenyl-;
wherein $R^6$ is
(a) H—,
(b) $(C_1-C_8$ alkyl)—,
(c) $(C_3-C_5$ cycloalkyl)—,
(d) phenyl-, or
(e) $OR^2$;
wherein $R^7$ is
(a) H—,
(b) $(C_1-C_8$ alkyl)—,
(c) $(C_3-C_5$ cycloalkyl)—,
(d) phenyl-,
(e) $H_2N$—,
(f) $H_2NCO$—,
(g) $R_5OCO$—,
(h) NC—,
(i) $R_5S$—,
(j) $R_5O$—, or
(k) $CF_3$;

with the following provisos:
where Q is XXV, $R^2$ and $R^3$ is H, $R^5$ is other than methyl;
where Q is XVIII, $R^2$ is other than phenyl;
wherein m is zero (0) to five (5), inclusive;
wherein n is zero (0) to two (2), inclusive;
wherein $Y^1$, $Y^2$, $Y^3$, and $Y^4$ are independently (a) H,
(b) $NO_2$, or
(c) F, Cl, or Br.

2. The compound of claim 1 wherein $X^1$ is fluorine.
3. The compound of claim 2 wherein $X^2$ is hydrogen.
4. The compound of claim 3 wherein $R^1$ is acetyl.
5. The compound of claim 1 which is:
   a) (S)—N—[[3-[3-Fluoro-4-[4-(2-oxazolyl)-1-piperazinyl]phenyl]-2-oxo-5-oxazolidinyl]methyl]acetamide (I-A);
   b) (S)—N—[[3-[3-Fluoro-4-[4-(4-oxo-2-oxazolinyl)-1-piperazinyl]phenyl]-2-oxo-5-oxazolidinyl]methyl]acetamide (I-B);
   c) (S)—N—[[3-[3-Fluoro-4-[4-(4,5-dihydro-2-oxazolyl)-1-piperazinyl]phenyl]-2-oxo-5-oxazolidinyl]methyl]acetamide (I-C);
   d) (S)—N—[[3-[4-[4-(2-Benzoxazolyl)-1-piperazinyl]-3-fluorophenyl]-2-oxo-5-oxazolidinyl]methyl]acetamide (I-D);
   e) (S)—N—[[3-[3-Fluoro-4-[4-(5-nitrobenzoxazol-2-yl)-1-piperazinyl]phenyl]-2-oxo-5-oxazolidinyl]methyl]acetamide (I-D);
   f) (S)—N—[[3-[3-Fluoro-4-[4-(5-fluorobenzoxazol-2-yl)-1-piperazinyl]phenyl]-2-oxo-5-oxazolidinyl]methyl]acetamide (I-D);
   g) (S)—N—[[3-[3-Fluoro-4-[4-(6-fluorobenzoxazol-2-yl)-1-piperazinyl]phenyl]-2-oxo-5-oxazolidinyl]methyl]acetamide (I-D);
   h) (S)—N—[[3-[3-Fluoro-4-[4-(7-fluorobenzoxazol-2-yl)-1-piperazinyl]phenyl]-2-oxo-5-oxazolidinyl]methyl]acetamide (I-D);
   i) (S)—N—[[3-[3-Fluoro-4-[4-(6,7-difluorobenzoxazol-2-yl)-1-piperazinyl]phenyl]-2-oxo-5-oxazolidinyl]methyl]acetamide (I-D);
   j) (S)—N—[[3-[3-Fluoro-4-[4-(1,3,4-oxadiazol-2-yl)-1-piperazinyl]phenyl]-2-oxo-5-oxazolidinyl]methyl]acetamide (I-E);
   k) (S)—N—[[3-[3-Fluoro-4-[4-(1,2,4-oxadiazol-5-yl)-1-piperazinyl]phenyl]-2-oxo-5-oxazolidinyl]methyl]acetamide (I-F);
   l) (S)—N—[[3-[3-Fluoro-4-[4-(1,2,4-oxadiazol-3-yl)-1-piperazinyl]phenyl]-2-oxo-5-oxazolidinyl]methyl]acetamide (I-G);
   m) (S)—N—[[3-[3-Fluoro-4-[4-(5-oxo-1,2,4-oxadiazol-3-yl)-1-piperazinyl]phenyl]-2-oxo-5-oxazolidinyl]methyl]acetamide (I-H);
   n) (S)—N—[[3-[3-Fluoro-4-[4-(2-oxo-1,3,4-oxathiazol-5-yl)-1-piperazinyl]phenyl]-2-oxo-5-oxazolidinyl]methyl]acetamide (I-I);
   o) (S)—N—[[3-[3-Fluoro-4-[4-(2-thiazolyl)-1-piperazinyl]phenyl]-2-oxo-5-oxazolidinyl]methyl]acetamide (I-J);
   p) (S)—N—[[3-[3-Fluoro-4-[4-(5-nitrothiazol-2-yl)-1-piperazinyl]phenyl]-2-oxo-5-oxazolidinyl]methyl]acetamide (I-J);
   q) (S)—N—[[3-[4-[4-(2-Benzothiazolyl)-1-piperazinyl]-3-fluorophenyl]-2-oxo-5-oxazolidinyl]methyl]acetamide (I-K);
   r) (S)—N—[[3-[3-Fluoro-4-[4-(6-nitrobenzothiazol-2-yl)-1-piperazinyl]phenyl]-2-oxo-5-oxazolidinyl]methyl]acetamide (I-K);
   s) (S)—N—[[3-[3-Fluoro-4-[4-(4-oxo-2-thiazolinyl)-1-piperazinyl]phenyl]-2-oxo-5-oxazolidinyl]methyl]acetamide (I-L);
   t) (S)—N—[[3-[4-[4-(4,5-Dioxo-2-thiazolinyl)-1-piperazinyl]-3-fluorophenyl]-2-oxo-5-oxazolidinyl]methyl]acetamide (I-M);
   u) (S)—N—[[3-[4-[4-(4,5-Dihydro-2-thiazolyl)-1-piperazinyl]-3-fluorophenyl]-2-oxo-5-oxazolidinyl]methyl]acetamide (I-N);
   v) (S)—N—[[3-[3-Fluoro-4-[4-(1,3,4-thiadiazol-2-yl)-1-piperazinyl]phenyl]-2-oxo-5-oxazolidinyl]methyl]acetamide (I-O);
   w) (S)—N—[[3-[3-Fluoro-4-[4-(5-oxo-1,3,4-thiadiazol-2-yl)-1-piperazinyl]phenyl]-2-oxo-5-oxazolidinyl]methyl]acetamide (I-P);
   x) (S)—N—[[3-[3-Fluoro-4-[4-(1,2,4-thiadiazol-5-yl)-1-piperazinyl]phenyl]-2-oxo-5-oxazolidinyl]methyl]acetamide (I-Q);
   y) (S)—N—[[3-[3-Fluoro-4-[4-(3-oxo-1,2,4-thiadiazol-5-yl)-1-piperazinyl]phenyl]-2-oxo-5-oxazolidinyl]methyl]acetamide (I-R);
   z) (S)—N—[[3-[3-Fluoro-4-[4-(1,2,5-thiadiazol-3-yl)-1-piperazinyl]phenyl]-2-oxo-5-oxazolidinyl]methyl]acetamide (I-S);
   aa) (S)—N—[[3-[3-Fluoro-4-[4-(1,2,3,4-thiatriazol-5-yl)-1-piperazinyl]phenyl]-2-oxo-5-oxazolidinyl]methyl]acetamide (I-T);
   bb) (S)—N—[[3-[3-Fluoro-4-[4-(3-oxo-1,2,4-dithiazol-5-yl)-1-piperazinyl]phenyl]-2-oxo-5-oxazolidinyl]methyl]acetamide (I-U);
   cc) (S)—N—[[3-[3-Fluoro-4-[4-(imidazol-2-yl)-1-piperazinyl]phenyl]-2-oxo-5-oxazolidinyl]methyl]acetamide (I-V);
   dd) (S)—N—[[3-[4-[4-(2-Benzimidazolyl)-1-piperazinyl]-3-fluorophenyl]-2-oxo-5-oxazolidinyl]methyl]acetamide (I-W);
   ee) (S)—N—[[3-[3-Fluoro-4-[4-(4-oxo-2-imidazolinyl)-1-piperazinyl]phenyl]-2-oxo-5-oxazolidinyl]methyl]acetamide (I-X);
   ff) (S)—N—[[3-[3-Fluoro-4-[4-(1,2,4-triazol-3-yl)-1-piperazinyl]phenyl]-2-oxo-5-oxazolidinyl]methyl]acetamide (I-Y, I-Z, and I-AA);
   gg) (S)—N—[[3-[3-Fluoro-4-[4-(3-oxo-1,2,4-triazol-5-yl)-1-piperazinyl]phenyl]-2-oxo-5-oxazolidinyl]methyl]acetamide (I-BB);
   hh) (S)—N—[[3-[3-Fluoro-4-[4-(1,2,3-triazol-5-yl)-1-piperazinyl]phenyl]-2-oxo-5-oxazolidinyl]methyl]acetamide (I-CC);
   ii) (S)—N—[[3-[4-[3-Fluoro-4-[(1-phenyl-5-tetrazolyl)-1-piperazinyl]phenyl]-2-oxo-5-oxazolidinyl]methyl]acetamide (I-DD);
   jj) (S)—N—[[3-[4-[3-Fluoro-4-[(2-methyl-5-tetrazolyl)-1-piperazinyl]phenyl]-2-oxo-5-oxazolidinyl]methyl]acetamide (I-EE);
   kk) (S)—N—[[3-[4-[3-Fluoro-4-[(3-oxo-7-isoindolyl)-1-piperazinyl]phenyl]-2-oxo-5-oxazolidinyl]methyl]acetamide (I-FF);
   ll) (S)—N—[[3-[4-[3-Fluoro-4-[(3-oxo-5-pyrazolinyl)-1-piperazinyl]phenyl]-2-oxo-5-oxazolidinyl]methyl]acetamide (I-GG);

mm) (S)—N—[[3-[4-[3-Fluoro-4-[(3,4-dihydropyrazol-5-yl)-1-piperazinyl]phenyl]-2-oxo-5-oxazolidinyl]methyl]acetamide (I-HH);

nn) (S)—N—[[3-[4-[3-Fluoro-4-[(3-pyrazolyl)-1-piperazinyl]phenyl]-2-oxo-5-oxazolidinyl]methyl]acetamide (I-II);

oo) (S)—N—[[3-[4-[3-Fluoro-4-[(3-indazolyl)-1-piperazinyl]phenyl]-2-oxo-5-oxazolidinyl]methyl]acetamide (I-JJ);

pp) (S)—N—[[3-[4-[4-[(3-Benzoisothiazolyl)-1-piperazinyl]-3-fluorophenyl]-2-oxo-5-oxazolidinyl]methyl]acetamide (I-KK);

qq) (S)—N—[[3-[3-Fluoro-4-[4-(isoxazol-3-yl)-1-piperazinyl]phenyl]-2-oxo-5-oxazolidinyl]methyl]acetamide (I-LL);

rr) (S)—N—[[3-[3-Fluoro-4-[4-(1,2,3-oxathiazol-5-yl)-1-piperazinyl]phenyl]-2-oxo-5-oxazolidinyl]methyl]acetamide, S-oxide (I-MM);

ss) (S)—N—[[3-[4-[4-[(7-Benzisoxazolyl)-1-piperazinyl]-3-fluorophenyl]-2-oxo-5-oxazolidinyl]methyl]acetamide (I-NN);

tt) (S)—N—[[3-[3-Fluoro-4-[4-(5-methyl-1,3,4-thiadiazol-2-yl)-1-piperazinyl]phenyl]-2-oxo-5-oxazolidinyl]methyl]acetamide;

uu) (S)—N—[[3-[4-[4-(5-Amino-1,3,4-thiadiazol-2-yl)-3-fluoro-1-piperazinyl]phenyl]-2-oxo-5-oxazolidinyl]methyl]acetamide;

vv) (S)—N—[[3-[4-[4-(5-Ethoxycarbonyl-1,3,4-thiadiazol-2-yl)-3-fluoro-1-piperazinyl]phenyl]-2-oxo-5-oxazolidinyl]methyl]acetamide;

ww) (S)—N—[[3-[3-Fluoro-4-[4-(5-trifluoromethyl-1,3,4-thiadiazol-2-yl)-1-piperazinyl]phenyl]-2-oxo-5-oxazolidinyl]methyl]acetamide;

xx) (S)—N—[[3-[4-[4-(5-Aminocarbonyl-1,3,4-thiadiazol-2-yl)-3-fluoro-1-piperazinyl]phenyl]-2-oxo-5-oxazolidinyl]methyl]acetamide;

yy) (S)—N—[[3-[4-[4-(5-Cyano-1,3,4-thiadiazol-2-yl)-3-fluoro-1-piperazinyl]phenyl]-2-oxo-5-oxazolidinyl]methyl]acetamide;

zz) (S)—N—[[3-[3-Fluoro-4-[4-(5-methylthio-1,3,4-thiadiazol-2-yl)-1-piperazinyl]phenyl]-2-oxo-5-oxazolidinyl]methyl]acetamide;

aaa) (S)—N—[[3-[3-Fluoro-4-[4-(3-methyl-1,2,4-thiadiazol-5-yl)-1-piperazinyl]phenyl]-2-oxo-5-oxazolidinyl]methyl]acetamide;

bbb) (S)—N—[[3-[3-Fluoro-4-[4-(2-phenyl-3-oxo-1,2,4-thiadiazol-5-yl)-1-piperazinyl]phenyl]-2-oxo-5-oxazolidinyl]methyl]acetamide;

ccc) (S)—N—[[3-[3-Fluoro-4-[4-(5-methyl-1,3,4-oxadiazol-2-yl)-1-piperazinyl]phenyl]-2-oxo-5-oxazolidinyl]methyl]acetamide;

ddd) (S)—N—[[3-[4-[4-(5-Ethyl-1,3,4-thiadiazol-2-yl)-1-piperazinyl]-3-fluorophenyl]-2-oxo-5-oxazolidinyl]methyl]acetamide;

eee) (S)—N—[[3-[3-Fluoro-4-[4-(5-propyl-1,3,4-thiadiazol-2-yl)-1-piperazinyl]-phenyl]-2-oxo-5-oxazolidinyl]methyl]acetamide;

fff) (S)—N—[[3-[3-Fluoro-4-[4-(5-(1-methyl)ethyl-1,3,4-thiadiazol-2-yl)-1-piperazinyl]-phenyl]-2-oxo-5-oxazolidinyl]methyl]acetamide; or ggg) (S)—N—[[3-[4-[4-(5-Cyclopropyl-1,3,4-thiadiazol-2-yl)-1-piperazinyl]-3-fluoro-phenyl]-2-oxo-5-oxazolidinyl]methyl]acetamide.

6. A method for treating bacterial infections in patients comprising:

administering to a patient in need thereof an effective amount of a compound of Formula I as shown in claim 1.

7. The method of claim 6 wherein said compound of Formula I is administered orally, parenterally or topically in a pharmaceutical composition.

8. The method of claim 7 wherein said compound is administered in an amount of from about 0.1 to about 100 mg/kg of body weight/day.

* * * * *